(12) United States Patent
Semmes et al.

(10) Patent No.: US 7,811,772 B2
(45) Date of Patent: Oct. 12, 2010

(54) APOLIPOPROTEIN A-II ISOFORM AS A BIOMARKER FOR PROSTATE CANCER

(75) Inventors: O. John Semmes, Newport News, VA (US); Gunjan Malik, Pittsburgh, PA (US); Michael D. Ward, Chesapeake, VA (US)

(73) Assignee: Eastern Virginia Medical School, Norfolk, VA (US)

( * ) Notice: Subject to any disclaimer, the term of this patent is extended or adjusted under 35 U.S.C. 154(b) by 170 days.

(21) Appl. No.: 11/794,838

(22) PCT Filed: Jan. 6, 2006

(86) PCT No.: PCT/US2006/000450

§ 371 (c)(1),
(2), (4) Date: Apr. 14, 2008

(87) PCT Pub. No.: WO2006/074360

PCT Pub. Date: Jul. 13, 2006

(65) Prior Publication Data

US 2008/0248500 A1    Oct. 9, 2008

Related U.S. Application Data

(60) Provisional application No. 60/642,332, filed on Jan. 6, 2005.

(51) Int. Cl.
| | |
|---|---|
| *G01N 33/53* | (2006.01) |
| *G01N 33/574* | (2006.01) |
| *C07K 16/00* | (2006.01) |
| *C12P 21/08* | (2006.01) |

(52) U.S. Cl. ............... 435/7.1; 435/7.23; 530/387.1; 530/387.7; 530/388.1; 530/389.1; 530/391.1

(58) Field of Classification Search ............ None
See application file for complete search history.

(56) References Cited

U.S. PATENT DOCUMENTS

| | | | |
|---|---|---|---|
| 5,242,828 | A | 9/1993 | Bergstrom et al. |
| 5,500,347 | A | 3/1996 | Moll et al. |
| 5,512,657 | A | 4/1996 | Van Aken et al. |
| 5,719,060 | A | 2/1998 | Hutchens et al. |
| 5,894,063 | A | 4/1999 | Hutchens et al. |
| 6,020,208 | A | 2/2000 | Hutchens et al. |
| 6,124,137 | A | 9/2000 | Hutchens et al. |
| 6,225,047 | B1 | 5/2001 | Hutchens et al. |
| 6,283,761 | B1 | 9/2001 | Joao |
| 6,329,209 | B1 | 12/2001 | Wagner et al. |
| 6,555,813 | B1 | 4/2003 | Beecher et al. |
| 6,579,719 | B1 | 6/2003 | Hutchens et al. |
| 2002/0138208 | A1 | 9/2002 | Paulse et al. |
| 2002/0193950 | A1 | 12/2002 | Gavin et al. |
| 2003/0004402 | A1 | 1/2003 | Hitt et al. |
| 2003/0032043 | A1 | 2/2003 | Pohl et al. |
| 2003/0055615 | A1 | 3/2003 | Zhang et al. |
| 2003/0073096 | A1 | 4/2003 | Bao et al. |
| 2003/0105000 | A1* | 6/2003 | Pero et al. ............ 514/12 |
| 2003/0119033 | A1 | 6/2003 | Mikolajczyk et al. |
| 2003/0207462 | A1 | 11/2003 | Kitagawa |
| 2003/0218130 | A1 | 11/2003 | Boschetti et al. |
| 2003/0224399 | A1 | 12/2003 | Reed et al. |
| 2004/0018519 | A1 | 1/2004 | Wright, Jr. |

FOREIGN PATENT DOCUMENTS

| | | |
|---|---|---|
| EP | 1300683 | 4/2003 |
| WO | WO-9324834 | 12/1993 |
| WO | WO-9859360 | 12/1998 |
| WO | WO-9859362 | 12/1998 |
| WO | WO-9951773 | 10/1999 |
| WO | WO-0019208 | 4/2000 |
| WO | WO-0029987 | 5/2000 |
| WO | WO-0056934 | 9/2000 |
| WO | WO-0066265 | 11/2000 |
| WO | WO-0131580 | 5/2001 |
| WO | WO-0136977 | 5/2001 |
| WO | WO-0171360 | 9/2001 |
| WO | WO-03031031 | 4/2003 |
| WO | WO-03040700 | 5/2003 |
| WO | WO-03091695 | 11/2003 |
| WO | WO-2004030511 | 4/2004 |

OTHER PUBLICATIONS

Boyd (The Basic Science of Oncology, 1992, McGraw-Hill, Inc., p. 379).*
Tockman et al (Cancer Res., 1992, 52:2711s-2718s).*
Pritzker (Clinical Chemistry, 2002, 48:1147-1150).*
The National Cancer Institute (Dictionary of Cancer Terms, stage, www.cancer.gov. Dec. 2009).*
Rudikoff et al. (PNAS, USA, 1982, 79: 1979-1983).*
Coleman et al. (Research in Immunology, 1994; 145(1): 33-36).*
Abaza et al. (Journal of Protein Chemistry, vol. 11, No. 5, 1992, pp. 433-444).*
Gussow et al. (1991, Methods in Enzymology 203:99-121).*
MacCallum et al. (J. Mol. Biol. (1996) 262, 732-745).*
Malik et al. (Proc. Amer. Assoc. Can. Res. Mar. 27-31, 2004 45:843).*
Usui et al. (Clinical Chimica Acta 317: 2002 133-143).*

(Continued)

*Primary Examiner*—Peter J Reddig
(74) *Attorney, Agent, or Firm*—Wilmer Cutler Pickering Hale and Dorr LLP

(57) ABSTRACT

The present invention provides a protein-based biomarker, ApoA-II isoform, that is useful in determining prostate cancer status in a patient. In particular, the biomarker of this invention is useful to classify a biological sample as prostate cancer or non-prostate cancer. The ability of ApoA-II to detect disease in patients with a normal prostate-specific antigen (PSA) makes the biomarker of this invention useful in identifying indolent disease. The biomarker can be detected by SELDI mass spectrometry, HPLC, PAGE and Western blotting.

14 Claims, 9 Drawing Sheets

OTHER PUBLICATIONS

Sambrook et al. (Molecular cloning: A Laboratory Manual, 2nd ed. Cold Spring Harbor Laboratory Press 1989, pp. 18.60-18.61).*
European Search Report, dated Jan. 30, 2009, EPO App 06717624.8.
PCT International Search Report for Application No. PCT/US06/00450 dated Oct. 5, 2006.
Aspinall, et al., J Urol, 154:622-628 (1995).
Ball, et al., Bioinformatics, 18:395-404 (2002).
Banez, et al., J Urol, 170:442-446 (2003).
Banks, et al., "Soluble forms of the adhesion molecule E-cadherin in urine," J Clin Pathol, vol. 48, pp. 179-180 (1995).
Barnathan, et al., "Immunohistochemical Localization of Defensin in Human Coronary Vessels," American Journal of Pathology, vol. 150, No. 3, pp. 1009-1020, Mar. 3, 1997.
Bisgaier and Glickman, Annu Rev Physiol, 45:625-636 (1983).
Blanco-Vaca, et al., J Lipid Res. 33:1785-1796 (1992).
Brewer, et al., Proc Natl Acad Sci USA, 69:1304-1308 (1972).
Carr, et al., "Integration of Mass Spectrometry in Analytical Biotechnology," Anal Chem, vol. 63, pp. 2802-2824 (1991).
Carr, S. and Roland, S., "Overview of Peptide and Protein Analysis by Mass Spectrometry," Current Protocols in Molecular Biology, Supplement 38, pp. 10.21.1-10.21.27 (1997).
Carter, N. Engl J Med., 350:2292-2294 (2004).
Celis, J., "A comprehensive protein resource for the study of bladder cancer: http://biobase.dk/cgi-bin/celis," Electrophoresis, vol. 20, pp. 300-309 (1999).
De Marzo, et al., Am J Pathol, 153:911-919 (1998).
Deterding, et al., Eletrophoresis, 23:2296-2305 (2002).
Dhom, J. Cancer Res Clin Oncol, 106:210-218 (1983).
Diaz, et al., Urology, 53:931-938 (1999).
Edelstein, et al., J Biol Chem, 257:7189-7195 (1982).
Freeman and Solomon, J Cell Biochem, 91:54-69 (2004).
Gambert, Geriatrics, 56:22-26 (2001).
Garnick, Annals of Internal Medicine, 118:803-818 (1993).
Garnick, Scientific American, 270:72-81 (1994).
Golijanin, et al., Detection of Bladder Tumors by Immunostaining of the Lewis X Antigen in Cells from Voided Urine, Adult Urology, vol. 46, No. 2, pp. 173-177 (1995).
Gordon, et al., J Biol Chem, 258:14054-14059 (1983).
Grizzle, et al., In: M. Hanausek, Walasze, Z. (ed.), John Walker's Methods in Molecular Medicine—Tumor Marker Protocols, pp. 161-179: Humana Press, Inc., Totowa, NJ (1998).
Grizzle, et al., In: M. Hanausek, Walasze, Z. (ed.), John Walker's Methods in Molecular Medicine—Turmor Marker Protocols, pp. 143-160: Humana Press, Inc., Totowa, NJ (1998).
Halachmi, et al., "Urine cytology, tumour markers and bladder cancer," British Journal of Urology, vol. 83, pp. 647-654 (1998).
Hansson, et al., Immunotechnology, (3-4):237-252 (1999).
Jahn, et al., FEBS Lett, 131:366-368 (1981).
Jaroff, Time (Apr. 1, 1996).
Karp, et al., Cancer Res., 56:5547-5556 (1996).
Klein, et al., "Expression of Cytokeratin 20 in Urinary Cytology of Patients with Bladder Carcinoma," American Cancer Society, pp. 349-354 (1998).
Koopman, et al., Clin Cancer Res, 10:860-868 (2004).
Kozak, et al., Proc Natl Acad Sci USA, 100:12343-12348 (2003).
Kuwata, H., "Bactericidal Domain of Lactoferrin: Detection, Quantitation, and Characterization of Lactoferrincin in Serum by SELDI Affinity Mass Spectrometry," Biochemical and Biophysical Research Communications, vol. 245, pp. 764-773 (1998).
Lackner, et al., J. Biol Chem, 260:703-705 (1985).
Lehrer, Br J Cancer, 78:1398 (1998).
Liu, B, et al., "Detection of Onco-Fetal Bladder Antigen in Urine of Patients with Transitional Cell Carcinoma," The Journal of Urology, vol. 137, pp. 1258-1261, Jun. 1987.
Lokeshwar, et al., "Tumor-associated Hyaluronic Acid: A New Sensitive and Specific Urine Marker for Bladder Cancer," Cancer Research, vol. 57, pp. 773-777, Feb. 15, 1997.
Lopez-Ottin, et al., Nature Reviews, 3:509-519 (2002).
Malik, et al., "Serum Levels of an Isoform of Apolipoprotein A-II as a Potential Marker for Prostate Cander," Clin. Cancer Res., vol. 11, No. 3, pp. 1073-1085, Feb. 1, 2005.

McCormack, et al., Urology, 45:729-744 (1995).
McDavid, et al., Public Health Rep, 119:174-186 (2004).
Merchant, et al., Electrophoresis, 21:1164-1167 (2000).
Mizukawa, N., et al., "Presence of Defensin in Epithelial Langerhans Cells Adjacent to Oral Carcinomas and Precancerous Lesions," Anticancer Research, vol. 19, pp. 2969-2972 (1999).
Mizukawa, N., et al., "Immunohistochemical Staining of Human α-Defensin-1 (HNP-1), in the Submandibular Glands of Patients with Oral Carcinomas," Anticancer Research, vol. 20, pp. 1125-1128 (2000).
Myers, et al., J Urol, 165:1027-1032 (2001).
Niederkofler, et al., J Lipid Res, 44:630-639 (2003).
Nord, et al., Eur J Biochem, 15:4269-4277 (2001).
Paweletz, D., "Rapid Protein Display Profiling of Cancer Progression Directly from Human Tissue Using a Protein Biochip," Drug Development Research, vol. 49, pp. 34-42 (2000).
Pham, et al., "Tumor-derived Hyaluronidase: A Diagnostic Urine Marker for High-Grade Bladder Cancer," Cancer Research, vol. 57, pp. 778-783, Feb. 15, 1997.
Platz, et al., J Cell Biochem, 91:553-571 (2004).
Poon, et al., Clin Chem, 49:752-760 (2003).
Porter, E., "Isolation of human intestinal defensins from ileal neobladder urine," FEBS Letters, vol. 434, pp. 272-276 (1998).
Protheroe, A., "Urinary concentrations of the soluble adhesion molecule E-cadherin and total protein in patients with bladder cancer," British Journal of Cancer, vol. 80, pp. 273-278 (1999).
Qureshi, et al., Neural Network of Analysis of Clinicopathological and Molecular Markers in Bladder Cancer, The Journal of Urology, vol. 163, pp. 630-633, Feb. 2000.
Rasmussen, H., et al., "Towards a Comprehensive Database of Proteins From the Urine of Patients With Bladder Cancer," Journal of Urology, vol. 155, No. 6, p. 2113-2119, Jun. 1996.
Rittenhouse, et al., Crit Rev Clin Lab Sci, 35:275-368 (1998).
Ronnmark, et al., J Immunol Methods, (1-2):199-211 (2002).
Sarosdy, et al., "Improved Detection of Recurrent Bladder Cancer Using the Bard BTA stat Test," Adult Urology, vol. 50, No. 3, pp. 349-353 (1997).
Scanu, et al., Ann NY Acad Sci, 348:160-173 (1980).
Scanu, et al., Biochem Biophys Acta, 351:341-347 (1974).
Schamhart, D., "The Bard® BTA Test: It's Mode of Action, Sensitivity and Specificity, Compared to Cytology of Voided Urine, in the Diagnosis of Superficial Bladder Cancer," European Urology, vol. 34, pp. 99-106 (1998).
Schaub, et al., "Urine protein profiling with surface-enhanced laser-desorption/ionization time-of-flight mass spectrometry," Kidney Int., vol. 65, pp. 323-332 (2004).
Schmetter, et al., "A Multicenter Trial Evaluation of the Fibrin/Fibrinogen Degradation Products Test for Detection and Monitoring of Bladder Cancer," The Journal of Urology, vol. 158, pp. 801-805, Sep. 1997.
Schmitz, et al., J Lipid Res, 24:1021-1029 (1983).
Selsted, et al., The Journal of Cell Biology, vol. 118, No. 4, pp. 929-936, Aug. 1992.
Snow, et al., "Artificial Neural Networks in the Diagnosis and Prognosis of Prostate Cancer: A Pilot Study," The Journal of Urology, vol. 152, pp. 1923-1926, Nov. 1994.
Soloway, et al., "Use of a New Tumor Marker, Urinary NMP22, in the Detection of Occult or Rapidly Recurring Transitional Cell Carcinoma of the Urinary Tract Following Surgical Treatment," The Journal of Urology, vol. 156, pp. 363-367, Aug. 1996.
Stein, et al., "Prognostic Markers in Bladder Cancer: A Contemporary Review of the Literature," The Journal of Urology, vol. 160, pp. 645-659, Sep. 1998.
Steiner, et al., "Detection of bladder cancer recurrence by microsatellite analysis of urine," Nature Medicine, vol. 3, No. 6, pp. 621-624, Jun. 1997.
Tailleux, et al., Atherosclerosis, 165:1-3 (2002).
Tang, et al., Mass Spectrom Rev, 23:34-44 (2004).
Taylor, Arch Pathol Lab Med, 102:113-121 (1978).
Thompson, et al., N Eng J Med, 350:2239-2246 (2004).
Trougakos and Gonos, The International Journal of Biochemistry & Cell Biology, 34:1430-1448 (2002).
Tsao, et al., J. Biol Chem, 260:15222-15231 (1985).

Vlahou, A., et al., "Development of a Novel Proteomic Approach for the Detection of Transitional Cell Carcinoma of the Bladder in Urine," American Journal of Pathology, vol. 158, No. 4, pp. 1491-1502, Apr. 1, 2001.

Vlahou, et al., Clin Breast Cancer, 4:203-209 (2003).

Vlahou, et al., Clinical Cancer Res, vol. 5, Supp. [S], pp. 3867, #688 (1999).

Vlahou, et al., Identification of protein changes in bladder cancer patient urines by PROTEINCHIP™ SELDI affinity mass spectrometry, Abstract, American Cancer Society, Twentieth Annual Seminar of Cancer Researches in Virginia, Eastern Virginia Medical School, Mar. 11, 2000.

Vogel, et al., J Cell Biochem, 54:299-308 (1994).

Wadsworth, et al., Arch Otolaryngol Head Neck Surg, 130:98-104 (2004).

Wadsworth, et al., Clin Cancer Res, 10:1625-1632 (2004).

Warden, et al., Proc Natl Acad Sci USA, 90:10886-10890 (1993).

Wiesner, Curr Pharm Biotechnol, 5:45-67 (2004).

Weng, et al., Proc Natl Acad Sci USA, 93:14788-14794 (1996).

Won, et al., Proteomics, 3:2310-2316 (2003).

Wright, Jr., et al., Prostate Cancer and Prostatic Diseases, 2:264-276 (1999).

Wright, Expert Rev Mol Diagn, 2:549-563 (2002).

Wulfkuhle, et al., Adv Exp Med Biol, 532:59-68 (2003).

Xiao, et al., "A novel biochip SELDI mass spectrometry immunoassay for quantitation of prostate specific membrane antigen (PSMA) in body fluids," Abstract, American Cancer Society, Twentieth Annual Seminar of Cancer Researchers in Virginia, Eastern Virginia Medical School, Mar. 11, 2000 & Abstract, American Association for Cancer Research Annual Conference, San Franciso, Apr. 2-5, 2000.

Xiao, et al., Dis Markers, 19:33-39 (2003).

Yang, D., et al., "β-Defensins: Linking Innate and Adaptive Immunity Through Dendritic and T Cell CCR6," Science, vol. 286, pp. 525-528 (1999).

Zagars, et al., Cancer, 73:1904-1912 (1994).

Zhang, et al., J Urol, 159:548-554 (1998).

Zhao, C., et al., "Widespread expression of beta-defensin hBD-1 in human secretory glands and epithelial cells," FEBS Letters, vol. 396, pp. 319-322 (1996).

Zhukov, et al., Lung Cancer, 40:267-279 (2003).

\* cited by examiner

APOLIPOPROTEIN A-II ISOFORM AS A BIOMARKER FOR PROSTATE CANCER

STATEMENT REGARDING FEDERALLY SPONSORED RESEARCH

This invention was made with government support under grant number CA85067 awarded by the National Cancer Institute Early Detection Research Network and a grant by the Virginia Prostate Center. The government has certain rights in the invention.

FIELD OF THE INVENTION

The invention relates generally to Apolipoprotein A-II (ApoA-II) and specifically to new isoforms of ApoA-II that are specific for prostate cancer and methods of using the new ApoA-II isoforms.

BACKGROUND OF THE INVENTION

Prostate cancer (PCa) is the most frequently diagnosed cancer in men in the United States, and is the second leading cause of male cancer deaths (Karp et al., Cancer Res, 56:5547-5556, 1996). One of every 10 men currently develops prostate cancer at some point in his life. Projections from autopsy surveys indicate that as many as 11 million American men have prostate cancer (Dhom, J Cancer Res Clin Oncol, 106:210-218, 1983). Further, the rate of appearance of prostate cancer in African-American men is 37% higher than for their white counterparts (Jaroff, Time, Apr. 1, 1996).

Due to this high prevalence of prostate cancer there has been a large-scale search for potential biomarkers useful in the early detection and prognosis of prostate cancer. The "gold standard" diagnostic marker for prostate cancer is prostate specific antigen (PSA). PSA is a member of the human kallikrein family of serine proteases (Rittenhouse et al., Crit Rev Clin Lab Sci, 35:275-368, 1998). PSA exists in the serum as the free form of PSA. However, the majority of the PSA is in a complex with α1-antichymotrypsin (ACT). More recently it has been demonstrated that the level of free or non-complexed PSA in serum can improve the discrimination of prostate cancer from benign prostatic hyperplasia (BPH). The rapid incorporation of aggressive PSA testing has resulted in a dramatic reduction in the identification of advanced stages of prostate cancer as well as deaths secondary to prostate cancer (McDavid et al., Public Health Rep, 119:174-186, 2004; Carter, N Engl J Med, 350:2292-2294, 2004).

In normal men PSA ranges from 0 to 4 nanograms/milliliters. The presence of PSA can be measured with relative ease from blood samples using standard antibody-based detection. Prostate enlargements, a condition known as benign prostatic hyperplasia (BPH), is found in about half of men over age 45. With BPH, PSA levels rise in proportion to prostate size, possibly obscuring diagnosis of prostate cancer. When PSA levels are usually in the range of 4-10 ng/ml the PSA test seems to lack specificity to distinguish between benign prostatic hyperplasia and prostate cancer without additional tests, such as digital rectal exam and/or prostate needle biopsy (McCormack et al., Urology, 45:729-744, 1995). In the majority of cases, PSA elevation is due to BPH or prostatitis rather than carcinoma. In addition, a significant proportion of men with prostate cancer have normal PSA levels. Thus, the PSA test is somewhat non-specific for distinguishing prostate cancer and BPH, and produces a degree of false negative results (Garnick, Am Inst Med, 118:804-818, 1993).

Further, the significantly high false positive rate of PSA combined with its widespread clinical application has lead to a tremendous increase in the number of unnecessary biopsies of the prostate (Gambert, Geriatrics, 56:22-26, 2001). In addition, recent reports, such as those from the Prostate Cancer Prevention Trial (PCPT) (Thompson et al., N Engl J Med, 350:2239-2246, 2004), highlight the inability of PSA to separate aggressive prostate cancer from clinically indolent disease (Platz et al., J Cell Biochem, 91:553-571, 2004). Such reports support the concept that no single marker will accurately reflect the complex phenotypic changes associated with development of cancer. There has been, therefore, an increasing emphasis on the need to determine multiple protein biomarkers for use in the diagnosis/prognosis of prostate cancer. The development of high-throughput methods that are able to analyze large segments of the proteome promise to facilitate the identification of multiple protein panels for cancer diagnostics.

Surface Enhanced Laser Desorption/Ionization time of flight mass spectrometry (SELDI-TOF-MS) is a useful tool for integrating separation and analysis of complex mixtures of proteins. The protein profiles are generated using specific surface chemistry to affinity capture proteins from complex biological mixtures. Captured proteins are then analyzed by TOF-MS, generating a spectral map depicting approximations of the molecular weight (mass/charge or m/z) and relative concentration (intensity) of each protein (ion). The technique is a convenient, high-throughput tool to segregate proteins from complex bodily fluids like serum and generate comparative protein profiles. SELDI technology has now been widely used for diagnosis of cancer and other diseases in a large number of studies (reviewed by Wiesner, Curr Pharm Biotechnol, 5:45-67, 2004; Tang et al., Mass Spectrom Rev, 23:34-44, 2004; Wulfkuhle et al., Adv Exp Med Biol, 532: 59-68, 2003; Wright, Expert Rev Mol Diagn, 2:549-563, 2002).

SELDI ProteinChip® technology has proven to be highly promising in cancer diagnostics (Grizzle et al., In: G. Patrinos, Ansorg, W. (ed.), Molecular Diagnostics, Vol. (in press), pp. In press: Elsevier Press, 2004). Vlahou et al. first demonstrated that using the spectral peaks of SELDI protein profiles significantly increases the sensitivity for detecting transitional cell carcinoma of the bladder (Vlahou et al., Am J. Pathol, 158:1491-1502, 2001). The application of a pattern recognition algorithm to the data from the protein profiles was reported to be successful for the identification of ovarian cancer (Petricoin et al., Lancet, 359:572-577, 2002). Subsequently, Qu et al. and Adam et al. demonstrated the utility of protein expression profiling using an automated decision tree algorithm as an accurate assay for the detection of prostate cancer (Qu et al., Clin Chem, 48:1835-1843, 2002; Adam et al., Cancer Res, 62:3609-3614, 2002).

Indeed, following these initial publications there have been numerous reports of the successful application of this approach to cancer diagnostics (Banez et al., J Urol, 170:442-446, 2003; Wadsworth et al., Arch Otolaryngol Head Neck Surg, 130:98-104, 2004; Wadsworth et al., Clin Cancer Res, 10: 1625-1632, 2004; Petricoin et al., J Natl Cancer Inst, 94:1576-1578, 2002; Vlahou et al., Clin Breast Cancer, 4:203-209, 2003; Ball et al., Bioinformatics, 18:395-404, 2002; Cazares et al., Clin Cancer Res, 8:2541-2552, 2002; Koopmann et al., Clin Cancer Res., 10:860-868, 2004; Kozak et al., Proc Natl Acad Sci USA, 100: 12343-12348, 2003; Li et al., Clin Chem, 48:1296-1304, 2002; Paweletz et al., Dis Markers, 17:301-307, 2001; Poon et al., Clin Chem, 49:752-760, 2003; Won et al., Proteomics, 3:2310-2316, 2003; Xiao et al., Dis Markers, 19:33-39, 2003; Zhukov et al., Lung Cancer, 40:267-279, 2003). In particular, WO 2004/030511 A2 (incorporated herein in its entirety by reference) describes the application of SELDI to identify protein biomarkers that may advantageously be utilized in diagnosing prostate cancer and benign prostate hyperplasia. The prostate cancer-specific biomarkers identified in WO 2004/030511 A2 have the following molecular weights (in Daltons) of about 3486+/−6; 3963+/−7; 4071+/−7; 4079+/−7; 4475+/−81; 4580+/−8; 5074+/−91; 5298+/−10; 5382+/−97, 6099+/−11; 6542+/−12; 6797+/−12; 6949+/−13; 6990+/−13; 7024+/−13; 7054+/−13; 7820+/−14; 7844+/−14; 7885+/−14; 8067+/−15; 8141+/−15; 8356+/−15; 8943+/−16; 9149+/−16; 9508+/−17; 9656+/−17; and 9720+/−18.

Similarly, biomarkers for detecting prostate cancer were identified in WO03091695 (incorporated herein by reference in its entirety). The prostate cancer-specific biomarkers identified in WO03091695 have the following molecular weights (in Daltons) of about 2,062; 2,540; 2,680; 2,790; 2,996; 3,160; 3,320; 3,936; 4,290; 4,658; 5,149; 5,861; 5,999; 6,158; 6,677; 6,722; 7,808; 7,974; 8,019; 10,300; 10,800; 12,700; 14,703; 14,576; 15,900; 16,100; 16,300; 17,900; 24,346; 28,098; 55,785; and 60,958.

However, none of the protein markers identified by mass in WO 2004/030511 A2 and WO03091695 was identified further. Thus, there is no information available as to the proteins to which these protein biomarkers relate to or by which gene they are encoded. Still, all of these findings strongly support the potential usefulness of profiling of protein expression, coupled with decision algorithms, for improving the early detection/diagnosis of prostate cancer.

Recent efforts have been undertaken to identify markers for prostate cancer. For example, U.S. Patent Application Pub. No. 2003/0073096 A1 (incorporated herein in its entirety by reference) describes the use of Pin1, an essential and highly conserved mitotic peptidyl-propyl isomerase (PPIase) that catalyzes the isomerization of only phosphorylated Ser/Thr-Pro bonds, as a marker for prostate cancer. In addition, U.S. Patent Application Pub. No. 2003/0119033 A1 (incorporated herein in its entirety by reference) describes a novel form of PSA. Further, U.S. Patent Application Pub. No. 2003/0224399 A1 (incorporated herein in its entirety by reference) discloses use of IAP (inhibitor of apoptosis) as a biomarker that is diagnostic for survival of a patient with a prostate neoplastic condition. U.S. Patent Application Pub. No. 2004/0018519 A1 describes the use of PSMA (prostate specific membrane antigen) as a prostate cancer marker. As no single biomarker may accurately portray the complexity of prostate cancer, it is important that additional diagnostic biomarkers be identified in order to reduce prostate cancer mortality.

There is clearly a need for new methods in the fight against prostate cancer and it would therefore be beneficial to provide specific methods and reagents for the diagnosis, staging, prognosis, and monitoring of prostate cancer. We addressed this need by profiling the protein expression in prostate cancer and by identifying the biomarkers represented by the subset of m/z peaks comprising a potential group of proteins expressed at elevated levels in prostate cancer. Specifically, we targeted m/z peaks for further identification that demonstrated significant AUC (area under the curve) for discriminating between any two groups (>0.7 for disease vs. non-disease) and were observed as clearly delineated well-expressed m/z peak events. Identification of these cancer biomarkers will assist in successful implementation of profiling-based diagnostics, as well as facilitate the development of more traditional multi-protein antibody array or multiplex immunoassays for the early detection of prostate cancer. It may also potentially help elucidate important steps in the prostate cancer disease process.

BRIEF SUMMARY OF THE INVENTION

While the present invention may be embodied in many different forms, several specific embodiments are discussed herein with the understanding that the present disclosure is to be considered only as an exemplification of the principles of the invention, and it is not intended to limit the invention to the embodiments illustrated.

It is an object of the present invention to provide methods for determining prostate cancer status in a subject. In one embodiment of the present invention, a method for determining prostate cancer status in a subject is provided, the method comprising the steps of (a) providing a biological sample from the subject; (b) contacting the biological sample with a biospecific capture reagent capable of capturing an ApoA-II isoform, the ApoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15, whereby the ApoA-II isoform is bound to the biospecific capture reagent; (c) determining the amount of the bound ApoA-II isoform; and (d) correlating the amount of the bound ApoA-II isoform to prostate cancer status.

In one embodiment of the present invention, the prostate cancer status is prostate cancer versus normal. Another prostate cancer status determined by the methods of the present invention includes prostate cancer versus benign prostate hyperplasia. In other embodiments of the present invention, the prostate cancer status is (i) determined as part of screening, diagnosis or prognosis of prostate cancer in the subject; (ii) determined as part of determining susceptibility of the subject to prostate cancer; (iii) determined as part of determining the stage or severity of prostate cancer in the subject; (iv) determined as part of identifying a risk for the subject of developing prostate cancer; or (v) determined as part of monitoring the effect of an anti-prostate cancer drug or a therapy administered to the subject diagnosed with prostate cancer.

The biological sample may be a human physiological fluid such as whole blood or serum. The biological sample may also be a human prostate tissue sample, such as a prostate cancer tissue sample or a benign prostate hyperplasia tissue sample.

In a preferred embodiment of the present invention, the biospecific capture reagent is attached to a solid support. The solid support can be a mass spectrometry probe. The biospecific capture reagent may comprise an antibody attached to the probe. The step of determining the amount of the bound ApoA-II may comprise detecting the bound ApoA-II isoform by laser desorption-ionization mass spectrometry.

The antibody may be selected from the group consisting of polyclonal antibodies, monoclonal antibodies, bispecific antibodies, human antibodies, humanized antibodies, chimeric antibodies, single chain antibodies, and active fragments thereof.

In another embodiment of the present invention, the method comprises the step of (e) comparing the amount of the ApoA-II isoform in the biological sample with the amount of an ApoA-II isoform in a biological sample from one or more subjects free from prostate cancer or with a previously determined reference range for an ApoA-II isoform in subjects free from prostate cancer.

Determining the amount of the bound ApoA-II isoform can be done by (i) detecting the bound ApoA-II isoform by laser desorption-ionization mass spectrometry; (ii) high-performance liquid chromatography (HPLC); or (iii) polyacylamide gel electrophoresis (PAGE). PAGE may be two-dimensional PAGE.

In one embodiment of the present invention, the method for determining prostate cancer status in a subject comprises the step of (e) contacting the biological sample with a biospecific capture reagent capable of capturing a prostate cancer-specific biomarker X, wherein the prostate cancer-specific biomarker X is different from the ApoA-II isoform.

In another preferred embodiment of the present invention, a method for determining prostate cancer status in a subject is provided, the method comprising the steps of (a) providing a biological sample from the subject; (b) detecting or determining absence, presence or amount of an ApoA-II isoform, the ApoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15; and (c) correlating the absence, presence or amount of the ApoA-II isoform to prostate cancer status. This method embraces the specifics outlined above.

It is an object of the present invention to provide kits for determining prostate cancer status.

In one embodiment of the present invention a kit for determining prostate cancer status is provided, the kit comprising (a) a solid support comprising at least one biospecific capture reagent attached thereto, wherein the biospecific capture reagent is capable of capturing an ApoA-II isoform, the ApoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15; and (b) instructions for using the solid support to detect the ApoA-II isoform. In a preferred embodiment, the solid support is a SELDI probe. The kit may further comprise (c) a container containing the ApoA-II isoform.

In another embodiment of the present invention a kit for determining prostate cancer status is provided, the kit comprising (a) a solid support comprising at least one biospecific capture reagent attached thereto, wherein the biospecific capture reagent is capable of capturing an ApoA-II isoform, the ApoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15; and (b) a container containing the ApoA-II isoform. The solid support comprising the biospecific capture reagent may be a SELDI probe.

In yet another embodiment of the present invention, a kit for determining prostate cancer status is provided, the kit comprising (a) an antibody capable of binding to an ApoA-II isoform, the ApoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15; (b) reagents for PAGE and Western blotting; and (c) instructions for using the antibody to detect the ApoA-II isoform.

It is another object of the present invention to provide software for classifying a prostate cancer status.

In one embodiment of the present invention, the software comprises (a) a code that accesses data attributed to a biological sample, the date comprising measurement of an ApoA-II isoform, the ApoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15; and (b) a code that executes a classification algorithm that classifies the prostate cancer status of the biological sample as a function of the measurement.

The present invention further provides a method comprising the step of (a) communicating to a subject a diagnosis relating to prostate cancer status determined from the correlation of an ApoA-II isoform in a sample from the subject, the ApoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15. The diagnosis may be communicated to the subject via a computer-generated medium.

In another preferred embodiment of the present invention, a purified biomolecule comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15, is provided.

DEFINITIONS

Figure 1:
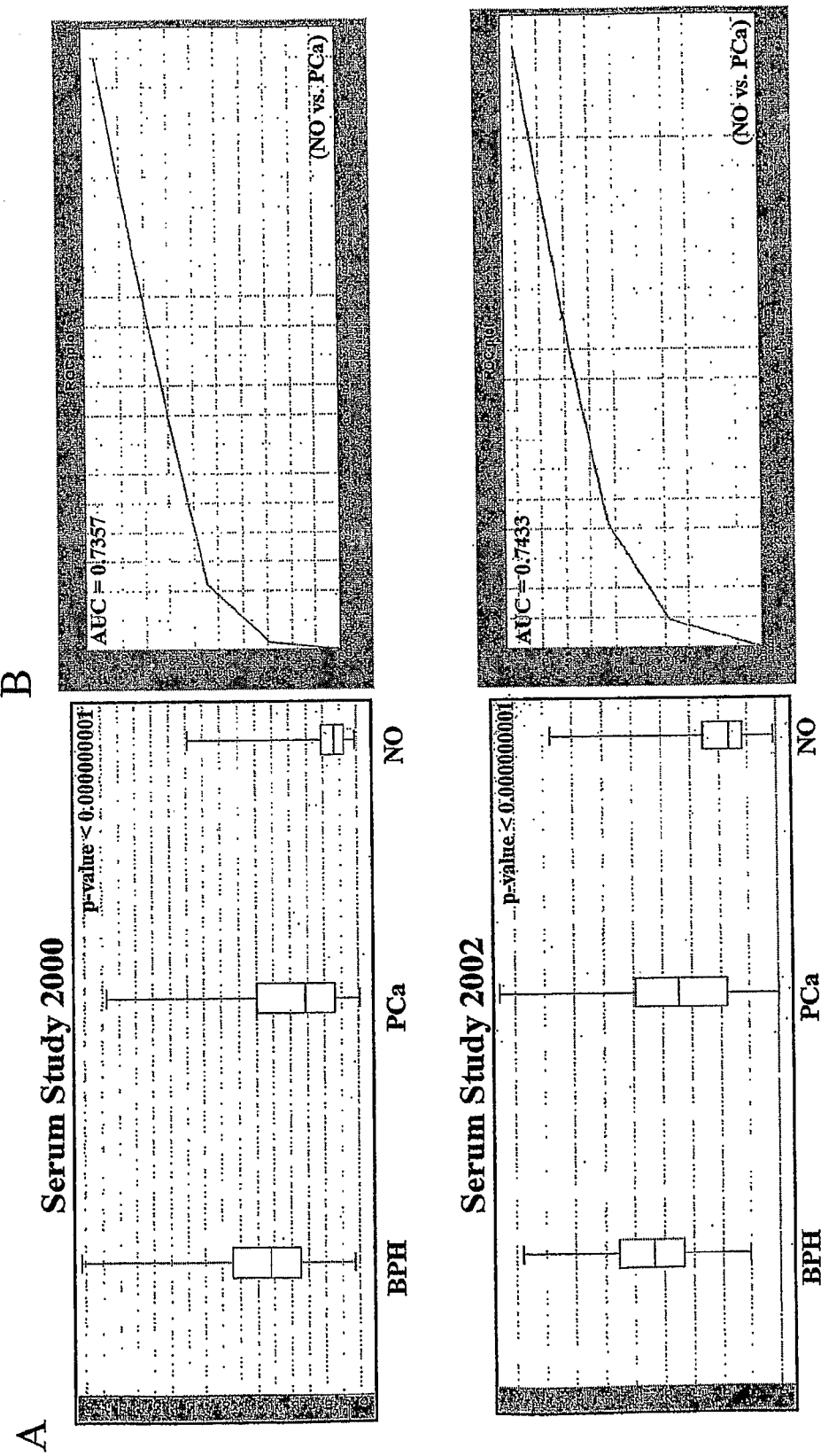
FIG. 1 shows the differential expression of an 8.9K m/z peak detected on IMAC-$Cu^{2+}$ ProteinChip® surface by SELDI-TOF MS. Panel A: Group box and whiskers cluster plot of the 8.9K m/z peak showing the relative normalized intensity in NO (Normal, Healthy), BPH (Benign Prostate Hyperplasia) and PCa (Prostate Cancer) sample groups in two independent serum studies conducted two years apart (Year 2000 and 2002). The horizontal lines forming the boxes and whiskers indicate statistical averages for the sample groups. Panel B: ROC statistics for NO vs. PCa analysis. An AUC >0.62 indicates the highly significant discriminatory value of the 8.9K m/z peak in these studies.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al., (eds.), Springer Verlag (1991); and Hale & Marham, The Harper Collins Dictionary of Biology (1991). As used herein, the following terms have the meanings ascribed to them unless specified otherwise.

"About" means approximately.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and o-phosphoserine. "Amino acid analog" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetic" refers to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Amino acid sequence" refers to the positional relationship of amino acid residues as they exist in a given peptide or protein.

"Antibody" refers to a protein functionally defined as a binding protein (a molecule able to bind to a specific epitope on an antigen) and structurally defined as comprising an amino acid sequence that is recognized by one of skill as being derived from the framework region of an immunoglobulin encoding gene. Structurally, the simplest naturally occurring antibody (e.g., IgG) comprises four polypeptides chains, two copies of a heavy (H) chain and two copies of a light (L) chain, all covalently linked by disulfide bonds. Specificity of binding is found in the variable (V) determinant of the H and L chains. Regions of the antibodies that are primarily structural are constant (C). The term "antibody" includes whole antibody, functional fragments, modifications or derivatives of the antibody. It can also be a genetically manipulated product, or bispecific antibody or chimeric antibody, such as a humanized antibody. Antibodies can be a polyclonal mixture or monoclonal. Antibodies can be intact immunoglobulins derived from natural sources or from recombinant sources and can be immunoreactive portions of intact immunoglobulins. Antibodies may exist in a variety of forms including, for example, Fv (consisting of the $V_L$ and $V_H$ domains of a single arm of an antibody), Fd (consisting of the $V_H$ and $C_{H1}$ domains), a dAB fragment (consisting of a $V_H$ domain; Ward et al., Nature, 341:544-546, 1989), an isolated complementary determining region (CDR), Fab (consisting of the $V_L$, $V_H$, $C_L$, and $C_{H1}$ domains, and F(ab)$_2$ (a bivalent fragment comprising two Fab fragments linked by a disulfide bridge at the hinge region) as well as in single chains. Single-chain antibodies (SCA), in which genes for a heavy chain and a light chain are combined into a single coding sequence, may also be used. Some SCA are genetically engineered molecules containing the variable region of the light chain, the variable region of the heavy chain, linked by a suitable polypeptide linker.

"Anti-prostate cancer drug" refers to a drug or medication given to a patient having prostate cancer for the purpose of treating prostate cancer.

"Apo" means Apolipoprotein; "ApoA-II" or "ApoA2" mean Apolipoprotein A-II. Apolipoprotein A-II is made as precursor protein of 100 amino acid residues (NCBI Accession Nos. NP_001634 and P02652). The fully processed ApoA-II contains 77 amino acid residues (NCBI Acession Nos. NP_001634 and P02652) and has a reported mass of 8.7 kDa (Gordon et al., J. Biol Chem, 258:14054-14059, 1983; Scanu et al., Biochem Biophys Acta, 351:341-347, 1974).

"ApoA-II isoform" refers to a peptide, polypeptide or protein derived from Apolipoprotein A-II. ApoA-II isoform includes polypeptides, peptides and proteins having complete or partial sequence identity with human Apolipoprotein A-II, but having a mass different from the reported mass of 8.7 kDa as has been reported by Gordon et al. (J. Biol Chem, 258: 14054-14059, 1983) and Scanu et al. (Biochem Biophys Acta, 351:341-347, 1974). Specifically included within this term are ApoA-II isoforms of ~8.8 kDa and of ~8.9 kDa, more specifically, 8943+/−15. Included within the term "ApoA-II isoform" are posttranslationally modified versions or fragments of an ApoA-II isoform.

"Benign prostate hyperplasia" or "benign prostatic hypertrophy" or "BPH" refer to an age-related non-cancerous (non-malignant) enlargement of the prostate. Symptoms usually include urinary urgency, frequency, and hesitancy, and penile erectile difficulties.

"Biological fluid" refers to a fluid from a host and includes whole blood, serum, plasma, urine, prostate fluid, tears, mucus ascites fluid, oral fluid, saliva, semen, seminal fluid, mucus, stool, sputum, cerebrospinal fluid, bone marrow, lymph and fetal fluid. The biological fluid samples may include cells, protein or membrane extracts of cells.

"Biological sample" refers to any sample obtained from a living or dead organism. Examples of biological samples include biological fluid and biological tissue specimens.

"Biomolecule" refers to an organic molecule and especially a macromolecule, such as a protein or nucleic acid. Included within protein are peptides, polypeptides or proteins comprising a polymer of amino acid residues. The term also applies to amino acid polymers in which one or more amino acid residue is an artificial chemical mimetic of a corresponding naturally occurring amino acid, as well as to naturally occurring amino acid polymers and non-naturally occurring amino acid polymer. Peptides, polypeptides and proteins of the present invention include amino acid polymers having D- and L-isoforms of individual amino acid residues, as well as other amino acid variants, as described herein. Peptides are distinguished by the number of amino acid residues making up the primary structure of the molecule. For purposes of this invention, peptides are those molecules comprising up to 50 amino acid residues, and polypeptides or proteins comprise 50 or more amino acid residues. However, methods of synthesis and/or delivery of peptides, polypeptides and proteins of the invention are similar, if not identical, as will be appreciated by one of skill in the art. Therefore, where appropriate, these terms are synonymous when discussing methods of synthesis, modification or use as therapeutic or diagnostic reagents.

"Biospecific capture reagent" refers to any material capable of capturing a marker, such as ApoA-II isoform. The term includes reagents comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific capture reagents are antibodies, receptor proteins and nucleic acids. A biospecific capture reagent of this invention includes a biospecific capture reagent that captures an ApoA-II isoform. The terms "biospecific capture reagent" and "biospecific adsorbent" are used interchangeably.

"Capture," "capturing" or grammatical equivalents thereof refer to the capability of a biospecific capture reagent to recognize and bind to a target molecule. Target molecule includes an ApoA-II isoform. Synonyms of the term "capture" are contemplated within the scope of the present invention and include, but are not limited to, adsorbing, preserving, keeping, holding, retaining. Generally it refers to a detectable binding between a biospecific capture reagent and a marker, such as ApoA-II isoform.

"Classification algorithm" refers to an algorithm that analyzes the data generated from mass spectrometry. It predicts whether or not an ApoA-II isoform in a particular biological sample is associated with a certain biological condition (e.g., prostate cancer versus non-prostate cancer).

"Code" in the context of software includes source code and machine code. Usually, the code is written by a programmer and readable by people but not computers. Source code must be converted to object code or machine language before a computer can read or execute the program.

"Computer-generated medium" means a system of worldwide electronic communication in which a computer user composes a message at one terminal that is generated at the recipient's terminal when he logs on. It includes email, a system for sending and receiving messages electronically over a computer network, as between personal computers.

"Correlating the amount" means comparing an amount of a substance, molecule or marker (such as ApoA-II isoform) that has been determined in one sample to a an amount of the same substance, molecule or marker determined in another sample. The amount of the same substance, molecule or marker determined in another sample may be specific for a given prostate cancer status.

Synonyms of the term "determining the amount" are contemplated within the scope of the present invention and include, but are not limited to, detecting, measuring, testing or determining, the presence, absence, amount or concentration of a molecule, such as an ApoA-II isoform.

"HPLC" means high-performance liquid chromatography.

"Laser desorption-ionization mass spectrometry" refers to a mass spectrometer which uses laser as a means to desorb, volatilize, and ionize a molecule. A mass spectrometer refers to a gas phase ion spectrometer that includes an inlet system, an ionization source, an ion optic assembly, a mass analyzer, and a detector.

The "molecular weight" of a polypeptide is given in Daltons or in kilo Daltons (kD).

"PAGE" means polyacrylamide gel electrophoresis and includes one-dimensional (1-D) PAGE and two-dimensional (2-D) PAGE.

"Probe" refers to a device that is removably insertable into a mass spectrometer and comprises a substrate or support having a surface, or one or more surface features, for presenting a marker, such as ApoA-II isoform, for detection. A probe can comprise a single substrate or support or a plurality of substrates or supports. Terms such as ProteinChip® array, biochip, or chip are also used herein to refer to specific kinds of probes.

"Prostate cancer" or "Pca" or "PCa" refers to an uncontrolled (malignant) growth of cells in the prostate gland. PCa is an adenocarcinoma of the prostate gland. The prostate gland is a walnut sized organ that helps the body form semen. The prostate gland is located where the urethea joins the neck of the urinary bladder. The term "prostate cancer" as used herein refers to both the appearance of a palpable tumor of the prostate, and also to microscopically detectable neoplastic or transformed cells in the prostate gland. In the latter case, the said cytologically-detectable prostate cancer may be asymptomatic, in that neither the patient nor the medical practitioner detects the presence of the cancer cells. Prostate cancer usually progresses gradually and usually expands to adjacent tissue and lymph glands before detection. In the event that prostate cancer metastasizes to additional sites distal to the prostate, the condition is described as metastatic cancer (MC), or prostate cancer, metastasized, to distinguish this condition from organ-defined prostate cancer.

"Prostate cancer status" includes any distinguishable manifestation of the disease, including non-disease. For example, disease status includes, without limitation, the presence or absence of disease (e.g., prostate cancer versus non-prostate cancer or prostate cancer versus benign prostate hyperplasia), the prostate cancer status as determined as part of screening, diagnosis or prognosis of prostate cancer in a subject, the susceptibility of a subject to prostate cancer, the risk of developing prostate cancer, the stage or severity of prostate cancer, the course of prostate cancer (e.g., progression of prostate cancer or regression of prostate cancer over time) and the effectiveness or response to treatment of prostate cancer, including monitoring the effect of an anti-prostate cancer drug or therapy administered to a subject diagnosed with prostate cancer. Based on this status, further procedures may be indicated, including additional diagnostic tests or therapeutic procedures or regimens.

"Purified" means substantially pure and refers to ApoA-II isoforms that are substantially free of other proteins, lipids, carbohydrates or other materials with which they are naturally associated. Purified ApoA-II isoforms may retain, however, covalent posttranslational modifications. The purified ApoA-II isoforms of the present invention will yield a single major peak by, for example, SELDI analysis. The purity of the ApoA-II isoform can also be determined by PAGE, amino-terminal amino acid sequence analysis and/or tryptic peptide analysis.

"SELDI" means surface enhanced laser desorption/ionization.

"Software" refers to application software and includes the programs, routines, procedures, rules and symbolic languages that control the functioning of the hardware and direct its operation. Software includes both source code written by humans executable machine code produced by assemblers or compilers.

"Solid support" or "solid phase" are used interchangeably and refer to a surface to which a biospecific capture reagent can attach.

"Subject" includes living and dead organisms. Examples of subjects include mammals, e.g., humans, dogs, cows, horses, pigs, sheep, goats, cats, mice, rabbits, rats, and transgenic nonhuman animals. Most preferably the subject is a human.

INCORPORATION BY REFERENCE

All publications, patents and patent applications cited in this specification are herein incorporated in their entireties by reference as if each individual publication, patent or patent application were specifically and individually indicated to be incorporated by reference.

DETAILED DESCRIPTION OF THE INVENTION

1. Introduction

A biomarker is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

2. Apolipoprotein A-II Isoform as a Biomarker for Prostate Cancer

This invention provides polypeptide-based biomarkers that are differentially present in subjects having prostate cancer, in particular, prostate cancer versus normal (non-prostate cancer). As defined herein, "normal" or "healthy" subjects are subjects with a negative diagnosis with respect to prostate cancer or BPH. Thus, normal individuals do not have prostate cancer or BPH. "Marker" or "biomarker" refers to an organic biomolecule, for example, a polypeptide (of a particular apparent molecular weight) or a nucleic acid, which is differentially present in a biological sample taken from a subject having prostate cancer or BPH as compared to a comparable biological sample taken from a normal or healthy subject. The term "differentially present" refers to differences in the quantity and/or frequency of a biomarker present in a biological sample taken from a subject having prostate cancer or BPH as compared to a comparable biological sample taken from a normal or healthy subject. For example, a biomarker can be a polypeptide which is present at an elevated level or at a decreased level in biological samples from subjects having prostate cancer or BPH as compared to comparable biological samples taken from normal or healthy subjects. Alternatively, a biomarker can be a polypeptide which is detected at a higher frequency or at a lower frequency in biological samples from subjects having prostate cancer or BPH as compared to comparable biological samples taken from normal or healthy subjects.

As used herein, the terms "high level" or "elevated" or "overexpression" of an ApoA-II isoform is related to a level of ApoA-II isoform above a determined reference level. The reference level may be different for each prostate cancer status. Thus, for example, in accordance with the present invention, a reference level of ApoA-II in a normal or healthy subject is identified as a cut-ff value, above which there is a significant correlation between the level of ApoA-II and a given prostate cancer status. Those of skill in the art will recognize that some cut-off values are not absolute in that clinical correlations are still significant over a range of values on either side of the cut-off.

The biomarkers may be characterized by mass-to-charge ratio as determined by mass spectrometry, by the shape of their spectral peak in time-of-flight mass spectrometry and by their binding characteristics to adsorbent surfaces. These characteristics provide one method to determine whether a particular detected biomolecule is a biomarker of this invention. These characteristics represent inherent characteristics of the biomolecules and not process limitations in the manner in which the biomolecules are discriminated.

In one aspect, this invention provides these biomarkers in isolated form. In one embodiment of the present invention, a purified biomolecule is provided, the biomolecule comprising (a) amino acid sequence VKSPELQAEAK (SEQ ID NO: 1) and (b) amino acid sequence SKEQLTPLIK (SEQ ID NO:2) and wherein the purified biomolecule has a molecular weight of about 8943 Dalton +/−15.

A purified biomolecule of this invention comprises amino acid sequences that are found in the amino acid sequence of human Apolipoprotein A-II precursor and mature human Apolipoprotein A-II polypeptide. Specifically, the amino acid sequence VKSPELQAEAK (SEQ ID NO: 1) of the purified biomolecule of the present invention is found at position 52 to 62 of the human Apolipoprotein A-II precursor and at position 29 to 39 of the mature human Apolipoprotein A-II polypeptide (NCBI Accession Nos. NP_001634 and P02652). The amino acid sequence SKEQLTPLIK (SEQ ID NO:2) of the purified biomolecule of the present invention is found at position 68 to 77 of the human Apolipoprotein A-II precursor and at position 45 to 54 of the mature human Apolipoprotein A-II polypeptide (NCBI Accession Nos. NP_001634 and P02652). A purified biomolecule comprising SEQ ID NO: 1 and SEQ ID NO:2 and having a molecular weight of 8943 Dalton +/−15 will be referred to as ApoA-II isoform. The reported mass of mature human Apolipoprotein A-II is 8.7 kDa (Gordon et al., J. Biol Chem, 258:14054-14059, 1983; Scanu et al., Biochem Biophys Acta, 351:341-347, 1974). ApoA-II isoforms discovered in this invention have molecular weights of ~8.8 kDa and of ~8.9 kDa, more specifically, 8943+/−15.

The ApoA-II isoform was discovered using SELDI technology employing ProteinChip arrays from Ciphergen Biosystems, Inc. (Fremont, Calif. ) ("Ciphergen"). Biological samples were collected from subjects diagnosed with prostate cancer and subjects diagnosed as normal. The samples were fractionated by anion exchange chromatography. Fractionated samples were applied to SELDI biochips and spectra of polypeptides in the samples were generated by time-of-flight mass spectrometry on a Ciphergen PBSII mass spectrometer. The spectra thus obtained were analyzed by Ciphergen Express™ Data Manager Software with Biomarker Wizard and Biomarker Pattern Software from Ciphergen Biosystems, Inc. The mass spectra for each group were subjected to scatter plot analysis. A Mann-Whitney test analysis was employed to compare prostate cancer and control groups for each protein cluster in the scatter plot, and proteins were selected that differed significantly (p<0.0001) between the two groups. This method is described in more detail in the Example Section.

The biomarkers of this invention are characterized by their mass-to-charge ratio as determined by mass spectrometry. Thus, for example, an ApoA-II isoform of this invention has a measured mass-to-charge ratio of 8943. The mass-to-charge ratios were determined from mass spectra generated on a Ciphergen Biosystems, Inc. PBS II mass spectrometer. This instrument has a mass accuracy of about +/−0.15 percent. Additionally, the instrument has a mass resolution of about 400 to 1000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII, taking the maximum and minimum mass-to-charge-ratio in the cluster, and dividing by two. Accordingly, the masses provided reflect these specifications.

The biomarkers of this invention are further characterized by their binding properties on chromatographic surfaces. Most of the biomarkers bind to cation exchange adsorbents (e.g., the Ciphergen® WCX ProteinChip® array) after washing with 100 mM sodium acetate at pH 4.

The identity of certain of the biomarkers of this invention has been determined as described in the Example Section. For biomarkers whose identity has been determined, such as for an ApoA-II isoform, the presence or amount of the biomarker can be determined by methods described herein and by other methods known in the art.

Biomarkers of this invention are initially characterized by mass-to-charge ratio, binding properties and spectral shape. Thus, they can be detected by mass spectrometry without knowing their specific identity. However, biomarkers can be identified by, for example, determining the amino acid sequence of the polypeptides. For example, a biomarker can be peptide-mapped with a number of enzymes, such as trypsin or V8 protease, and the molecular weights of the digestion fragments can be used to search databases for sequences that match the molecular weights of the digestion fragments generated by the various enzymes. Alternatively, protein biomarkers can be sequenced using tandem MS technology. In this method, the protein is isolated by, for example, gel electrophoresis. A band containing the biomarker is cut out and the protein is subject to protease digestion. Individual protein fragments are separated by a first mass spectrometer. The fragment is then subjected to collision-induced cooling, which fragments the peptide and produces a polypeptide ladder. A polypeptide ladder is then analyzed by the second mass spectrometer of the tandem MS. The difference in masses of the members of the polypeptide ladder identifies the amino acids in the sequence. An entire protein can be sequenced this way, or a sequence fragment can be subjected to database mining to find identity candidates. For example, further analysis the biomarker M8943 demonstrated that the tryptic peptides thereof are identical to amino acid sequences found in human Apolipoprotein A-II. Thus, M8943 could be identified as an ApoA-II isoform.

The ApoA-II isoform biomarkers of this invention are biomolecules. Accordingly, this invention provides these biomolecules in purified form. An ApoA-II isoform biomarker can be isolated and purified from biological fluids, such as urine or serum. They can be isolated by any method known in the art, based on their mass, their binding characteristics and their identity as an ApoA-II isoform polypeptide. For example, a biological sample comprising the biomolecules can be subject to chromatographic fractionation, as described herein, and subject to further separation by, e.g., acrylamide gel electrophoresis. Knowledge of the identity of the biomarker also allows their isolation by immunoaffinity chromatography.

3. Providing a Biological Sample from a Subject

Beyond detection of elevated PSA levels other current methods for diagnosing and staging prostate cancer are known to medical practitioners skilled in the art and include rectal examination, transrectal ultrasonography (TRUS) or magnetic resonance imaging (MRI), bone scanning, X-rays, skeletal muscle survey, intravenous pyelography, CAT-scan, and biopsy (reviewed in Garnick, Annals of Internal Medicine, 118:803-818, 1993; Garnick, Scientific American 270: 72-81, 1994). However, a more convenient and often more accurate way to diagnose and stage prostate cancer would be to characterize a biological sample from a subject.

In an embodiment of the present invention, a biological sample is provided from a subject identified as having a prostate abnormality. Alternatively, biological samples may be obtained from a subject not having been identified as having a prostate abnormality. The biological sample may be a biological fluid or a tissue specimen.

3.1. Biological Fluids

For the purpose of the present invention, the biological fluid can be any physiological fluid sample as defined herein, preferably a mammalian physiological fluid sample, most preferably a human physiological fluid sample. In a preferred embodiment of the present invention, the biological fluid for detection of an ApoA-II isoform biomarker is serum. Another preferred biological fluid is whole blood. However, in another embodiment, an ApoA-II isoform biomarker can be detected in urine.

3.2. Tissue Specimens

The biological sample may be a tissue specimen. Thus, in one embodiment of the present invention the ApoA-II isoform biomarker is detected in a tissue specimen from a subject. Examples of tissue specimen useful to practice the methods of the present invention include samples taken from the prostate, central nervous system, bone, breast tissue, renal tissue, endometrium, head/neck, gall bladder, parotid tissue, brain, pituitary gland, kidney tissue, muscle, esophagus, stomach, small intestine, colon, urethea, liver, spleen, pancreas, thyroid tissue, heart, lung, bladder, adipose tissue, lymph node tissue, adrenal tissue, testis tissue, tonsils, and thymus. Preferably, the biological sample is a prostate tissue sample, most preferably a human prostate tissue sample. In a preferred embodiment of the present invention, the human prostate tissue sample is a prostate cancer tissue sample. The prostate cancer tissue sample may be from any of the prostate cancer stages described herein. In another preferred embodiment, the human prostate tissue sample is a benign prostate hyperplasia tissue sample.

The prostate is composed of three different types of prostate tissue: the central zone, the peripheral zone (PZ) and the transition zone (TZ). The PZ comprises about 70% of the volume of a normal prostate, while the central zone and TZ are about 25% and 5%, respectively. All three zones are well defined in the art (See Bostwick and Dundore, *Biopsy Pathology of the Prostate*, published by Chapman & Hall USA, 115 Fifth Ave., New York, N.Y., 10003). Briefly, the TZ is characterized by small, simple glands embedded in a compact stroma, whereas the PZ is characterized by small glands embedded in a loose stroma. The TZ tissue forms a distinctive boundary with the PZ.

It is the TZ which becomes hyperplastic in patients with BPH. With extensive BPH, the TZ grows to several times the volume of other prostate zones. The TZ tissue surrounds the proximal prostate urethea, which is the reason that restricted urinary flow is a symptom of enlarged TZ resulting from BPH. In contrast, most cancers are found in the peripheral zone. Thus, in the prostate of a prostate cancer patient usually a non-cancerous peripheral zone tissue (N-PZ), a cancerous peripheral zone tissue containing tumor cells (C-PZ) and a non-cancerous transitional zone tissue (TZ) can be identified. The present invention discovers that anti ApoA-II antibodies detect different amounts of ApoA-II isoforms in different types of prostate tissues (see FIG. 5).

The ApoA-II isoforms of the present invention may also be used as an immunohistological marker to help distinguish cancer tissues from BPH or normal tissues. In accordance with the present invention, an ApoA-II isoform of the present invention may be detected in patient tissue samples by immunohistochemical assay procedures. Immunohistochemical methods for the detection of antigens in patient tissue specimens are well known in the art and need not be described herein (Taylor, Arch Pathol Lab Med 102:113-121, 1978).

4. Contacting the Biological Sample with a Biospecific Capture Reagent

4.1. Biospecific Capture Reagents

ApoA-II isoform biomarkers of the present invention can be initially detected by any methodology that can detect and distinguish the ApoA-II isoform from the mature ApoA-II as described by Gordon et al. (J Biol Chem, 258:14054-14059, 1983) and Scanu et al. (Biochim Biophys Acta, 351:341-347, 1974). A biological sample suspected of containing an ApoA-II isoform of the present invention is contacted with a biospecific capture reagent capable of capturing the ApoA-II isoform, the ApoA-II isoform comprising (i) the amino acid sequence VKSPELQAEAK (SEQ ID NO:1) and (ii) the amino acid sequence SKEQLTPLIK (SEQ ID NO:2) and wherein the ApoA-II isoform has a molecular weight of about 8943 Dalton +/−15.

A preferred method for initial detection involves first capturing an ApoA-II isoform biomarker, e.g., with biospecific capture reagents, and then detecting the captured proteins by mass spectrometry. More specifically, the proteins are captured using biospecific capture reagents, such as antibodies, aptamers or affibodies that recognize the ApoA-II isoform biomarker. Aptamers include double-stranded DNA or single stranded RNA molecules that bind to specific molecular targets, such as proteins or metabolites. Affibodies, protein binding polypeptides that can be selected to desired target proteins, such as ApoA-II isoforms, can be isolated from combinatorial protein libraries (Hansson et al., Immunotechnology, (3-4):237-252, 1999; Nord et al., Eur J Biochem, 15:4269-4277, 2001; Ronnmark et al., J Immunol Methods, (1-2):199-211, 2002). This method also will also result in the capture of ApoA-II isoform interactors that are bound to the ApoA-II isoform or that are otherwise recognized by antibodies and that, themselves, can be biomarkers.

This invention contemplates traditional immunoassays including, for example, sandwich immunoassays including ELISA or fluorescence-based immunoassays, as well as other enzyme immunoassays. In the SELDI-based immunoassay, a biospecific capture reagent for the biomarker is attached to the surface of an MS probe, such as a pre-activated Protein-Chip array. The ApoA-II isoform biomarker is then specifically captured on the biochip through this reagent, and the captured ApoA-II isoform biomarker is detected by mass spectrometry.

The probe can be in the form of a wide variety of desired shapes, including circular, elliptical, square, rectangular, or other polygonal or other desired shape, as long as it can be inserted into a mass spectrometer. The probe can be made from a wide variety of materials that can support various biospecific capture reagents. Exemplary materials include insulating materials, such as glass and ceramic; semi-insulating materials, such as silicon wafers; electrically-conducting materials (including metals such as nickel, brass, steel, aluminum, gold or electrically conductive polymers); organic polymers; biopolymers, or combinations thereof.

4.1.1. Antibodies

The biospecific capture reagent may be any molecule capable of binding to the ApoA-II isoform. In a preferred embodiment, the capture reagent is an antibody. Thus, in a preferred embodiment of the present invention assessing the amount of ApoA-II isoform in a biological sample from a subject comprises contacting the biological sample with an antibody reactive to an ApoA-II isoform or a fragment thereof. The amount of binding of the antibody to the biological sample may be determined and compared to a predetermined base level.

The antibody may be selected from the group consisting of polyclonal antibodies, monoclonal antibodies, bispecific antibodies, human antibodies, humanized antibodies, chimeric antibodies, single chain antibodies, and active fragments thereof. Active fragments include, but are not limited to, Fv, Fd, dAB, CDR, Fab, and $Fab_2$.

"Antibody reactive to ApoA-II isoform" means that the antibody has an area on its surface or in a cavity which specifically binds to a particular portion of ApoA-II isoform, i.e., it has a binding affinity (usually expressed as Ka) for the ApoA-II isoform.

In another aspect of the present invention, an antibody that is specifically immunoreactive with and binds to an ApoA-II isoform of the present invention is provided. The term "specifically immunoreactive" as used herein indicates that the antibodies of the present invention preferentially recognize and bind to an ApoA-II isoform of the present invention over the mature ApoA-II as described by Gordon et al. (J. Biol Chem, 258:14054-14059, 1983) and Scanu et al. (Biochem Biophys Acta, 351:341-347, 1974). The term "preferentially recognize and bind" as used herein means that the antibodies of the present invention bind more tightly to an ApoA-II isoform of the present invention than to the mature ApoA-II as described by Gordon et al. (J. Biol Chem, 258:14054-14059, 1983) and Scanu et al. (Biochem Biophys Acta, 351:341-347, 1974). The cross reactivity of anti ApoA-II isoform antibodies to the mature form of ApoA-II is relatively low, preferably less than about 10%, and most preferably less than about 1%.

Alternatively, instead of using antibodies that preferentially recognize and bind to an ApoA-II isoform of the present invention, antibodies immunoreactive with and binding to Apolipoprotein A-II may be used in the methods of the present invention. Some of those antibodies are also useful for capturing ApoA-II isoforms (see Examples). The bound ApoA-II isoforms may then be further analyzed by, for example SELDI, other mass spectrometry techniques, and/or PAGE.

Polyclonal and monoclonal antibodies or active fragments thereof specifically immunoreactive with and binding to an ApoA-II isoform of this invention can be made from an antigen containing an ApoA-II isoform or a fragment thereof by methods well known to the skilled artisan (Harlow et al., *Antibodies: A Laboratory Manual*, Cold Spring Harbor Laboratory, 1988; Coligan et al., *Current Protocols in Immunology*, Wiley Interscience, 1991; all incorporated by reference). Thus, the ApoA-II isoform of the present invention can be used as an immunogen that is capable of eliciting a monoclonal antibody which preferentially recognizes and binds to an ApoA-II isoform of the present invention. An immunogen of the present invention may include an ApoA-II isoform as described herein or a fragment thereof.

The present invention also provides a hybridoma cell line that is capable of producing a monoclonal antibody that preferentially recognizes and binds an ApoA-II isoform of the present invention over mature ApoA-II as described by by Gordon et al. (J. Biol Chem, 258:14054-14059, 1983) and Scanu et al. (Biochem Biophys Acta, 351:341-347, 1974).

4.2. Biospecific Capture Agent Attached to Solid Support

Preferably, the biospecific capture reagents are bound to a solid phase. Then, the captured proteins can be detected by SELDI mass spectrometry or by eluting the proteins from the capture reagent and detecting the eluted proteins by traditional MALDI or by SELDI. The use of mass spectrometry is especially attractive because it can distinguish and quantify modified forms of a protein based on mass and without the need for labeling.

The biospecific capture reagent can be attached to many different solid supports. Solid supports may be of any shape or form. Examples of solid supports include, but are not limited to, a bead, a membrane, a chip or a plate, such as microtiter plate. Solid supports may be made, for example, of glass, polysterene, polypropylene, polyethylene, dextran, nylon, natural and modified celluloses, polyacrylamides, agaroses and magnetites.

Methods of coupling biospecific capture agents, such as antibodies, to a solid phase are well known in the art. They can employ, for example, bifunctional linking agents, or the solid phase can be derivatized with a reactive group, such as an epoxide or an imidizole, that will bind the molecule on contact. Biospecific capture reagents against different target proteins, including ApoA-II isoforms, can be mixed in the same place, or they can be attached to solid phases in different physical or addressable locations. For example, one can load multiple columns with derivatized beads, each column able to capture a single protein cluster. Alternatively, one can pack a single column with different beads derivatized with capture reagents against a variety of protein clusters, thereby capturing all the analytes in a single place. Accordingly, antibody-derivatized bead-based technologies, such as xMAP technology of Luminex (Austin, Tex.) can be used to detect the protein clusters. However, the biospecific capture reagents must be specifically directed toward the members of a cluster in order to differentiate them.

In yet another embodiment, the surfaces of biochips can be derivatized with the biospecific capture reagents directed against protein clusters either in the same location or in physically different addressable locations. One advantage of capturing different clusters in different addressable locations is that the analysis becomes simpler.

In a preferred embodiment of the methods of the present invention, wherein the solid support is a mass spectrometry probe and the biospecific capture reagent comprises an antibody attached to the probe, determining the amount of bound ApoA-II isoform comprises detecting the bound ApoA-II isoform by laser desorption-ionization mass spectrometry.

5. Detecting an ApoA-II Isoform Biomarker

After identification of the ApoA-II isoform and correlation with the clinical parameter of interest, the ApoA-II isoform of the present invention can be used as a biomarker in any of the methods of this invention. At this point, detection of the ApoA-II isoform can be accomplished by any specific detection methodology including affinity capture followed by mass spectrometry, or traditional immunoassay directed specifically the ApoA-II isoform as described herein.

Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

5.1. Biochips

In one embodiment, a biological sample is analyzed by means of a biochip. Biochips generally comprise solid substrates or solid supports and have a generally planar surface, to which a biospecific capture reagent (also called an adsorbent or affinity reagent) is attached. Frequently, the surface of a biochip comprises a plurality of addressable locations, each of which has the capture reagent bound there.

Protein biochips are biochips adapted for the capture of polypeptides. Many protein biochips are described in the art. These include, for example, protein biochips produced by Ciphergen Biosystems, Inc. (Fremont, Calif.), Packard BioScience Company (Meriden Conn.), Zyomyx (Hayward, Calif.), Phylos (Lexington, Mass.) and Biacore (Uppsala, Sweden). Examples of such protein biochips and their use are described in the following patents or published patent applications, which are incorporated hereby by reference in their entireties: U.S. Pat. No. 6,225,047; PCT International Publication No. WO 99/51773; U.S. Pat. No. 6,329,209, PCT International Publication No. WO 00/56934 and U.S. Pat. No. 5,242,828.

5.2. Detection by Mass Spectrometry

In a preferred embodiment, an ApoA-II isoform biomarker of the present invention is detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer.

5.2.1. SELDI

A preferred mass spectrometric technique for use in the invention is "Surface Enhanced Laser Desorption and Ionization" or "SELDI," as described, for example, in U.S. Pat. No. 5,719,060 and No. 6,225,047, both to Hutchens and Yip. This refers to a method of desorption/ionization gas phase ion spectrometry (e.g., mass spectrometry) in which an analyte (here, one or more of the ApoA-II isoform biomarkers) is captured on the surface of a SELDI mass spectrometry probe. There are several versions of SELDI.

One version of SELDI is called "affinity capture mass spectrometry." It also is called "Surface-Enhanced Affinity Capture" or "SEAC". This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent may be attached directly to the substrate or support of the selective surface, or the substrate or support may have a reactive surface that carries a reactive moiety that is capable of binding the capture reagent, e.g., through a reaction forming a covalent or coordinate covalent bond. Epoxide and acyl-imidizole are useful reactive moieties to covalently bind polypeptide capture reagents such as antibodies or cellular receptors. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen ProteinChip® arrays include NP20 (hydrophilic); H4 and H50 (hydrophobic); SAX-2, Q-10 and LSAX-30 (anion exchange); WCX-2, CM-10 and LWCX-30 (cation exchange); IMAC-3, IMAC-30 and IMAC 40 (metal chelate); and PS-10, PS-20 (reactive surface with acyl-imidizole, expoxide) and PG-20 (protein G coupled through acyl-imidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities that adsorb transition metal ions, such as copper, nickel, zinc, and gallium, by chelation. Preactivated ProteinChip arrays have acyl-imidizole or epoxide functional groups that can react with groups on proteins for covalent binding.

Such biochips are further described in: U.S. Pat. No. 6,579,719 (Hutchens and Yip, "Retentate Chromatography," Jun. 17, 2003); PCT International Publication No. WO 00/66265 (Rich et al., "Probes for a Gas Phase Ion Spectrometer," Nov. 9, 2000); U.S. Pat. No. 6,555,813 (Beecher et al., "Sample Holder with Hydrophobic Coating for Gas Phase Mass Spectrometer," Apr. 29, 2003); U.S. Patent Application No. U.S. 2003 0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Patent Application No. US 2003/0218130 A1 (Boschetti et al., "Biochips With Surfaces Coated With Polysaccharide-Based Hydrogels," Apr. 14, 2003) and U.S. Patent Application No. 60/448,467, entitled "Photocrosslinked Hydrogel Surface Coatings" (Huang et al., filed Feb. 21, 2003); all incorporated herein by reference in their entireties.

In general, a probe with an adsorbent surface is contacted with the biological sample for a period of time sufficient to allow an ApoA-II isoform biomarker that may be present in the sample to bind to the adsorbent. After an incubation period, the probe is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate or support with the bound biomarkers.

An ApoA-II isoform biomarker bound to the probe is detected in a gas phase ion spectrometer such as a time-of-flight mass spectrometer. The ApoA-II isoform biomarker is ionized by an ionization source such as a laser, the generated ions are collected by an ion optic assembly, and then a mass analyzer disperses and analyzes the passing ions. The detector then translates information of the detected ions into mass-to-charge ratios. Detection of an ApoA-II isoform biomarker typically will involve detection of signal intensity. Thus, both the quantity and mass of the ApoA-II isoform biomarker can be determined.

Another version of SELDI is Surface-Enhanced Neat Desorption (SEND), which involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyacetophenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-ethoxy)silyl propyl methacrylate. In another embodiment, the composition is a co-polymer of α-cyano-4-methacryloyloxycinnamic acid and octadecylmethacrylate ("C18 SEND"). SEND is further described in U.S. Pat. No. 6,124,137 and PCT International Publication No. WO 03/64594 (Kitagawa, "Monomers And Polymers Having Energy Absorbing Moieties Of Use In Desorption/Ionization Of Analytes," Aug. 7, 2003), incorporated herein by reference in their entireties.

SEAC/SEND is a version of SELDI in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

Another version of SELDI, called Surface-Enhanced Photolabile Attachment and Release (SEPAR), involves the use of probes having moieties attached to the surface that can covalently bind an analyte, and then release the analyte through breaking a photolabile bond in the moiety after exposure to light, e.g., to laser light (see, U.S. Pat. No. 5,719,060, incorporated herein by reference in its entirety). SEPAR and other forms of SELDI are readily adapted to detecting a biomarker or biomarker profile, pursuant to the present invention.

5.2.2. Other Mass Spectrometry Methods

In another mass spectrometry method, ApoA-II isoform biomarkers can be first captured on a chromatographic resin having chromatographic properties that bind the ApoA-II isoform biomarkers. In the present example, this could include a variety of methods. For example, one could capture the ApoA-II isoform biomarkers on a cation exchange resin, such as CM Ceramic HyperD F resin, wash the resin, elute the ApoA-II isoform biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the ApoA-II isoform biomarkers on an immuno-chromatographic resin that comprises antibodies that bind the ApoA-II isoform biomarkers, wash the resin to remove unbound material, elute the ApoA-II isoform biomarkers from the resin and detect the eluted ApoA-II isoform biomarkers by MALDI or by SELDI.

5.2.3. Data Analysis

Analysis of analytes, such as ApoA-II isoform biomarkers, by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation to generate a mass spectrum, baseline subtraction to eliminate instrument offsets and high frequency noise filtering to reduce high frequency noise.

Data generated by desorption and detection of ApoA-II isoform biomarkers can be analyzed with the use of a programmable digital computer. The computer program analyzes the data to indicate the number of biomarkers, such as ApoA-II isoforms, detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference. The reference can be background noise generated by the instrument and chemicals such as the energy absorbing molecule which is set at zero in the scale.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte, such as an ApoA-II isoform. Peak selection can be done visually, but software is available, as part of Ciphergen's ProteinChip® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

5.2.4. General Protocol for SELDI Detection of ApoA-II isoform Biomarkers for Prostate Cancer A preferred protocol for the detection of an ApoA-II isoform of this invention is as follows. The biological sample to be tested, e.g., serum or urine, preferably is subject to pre-fractionation before SELDI analysis. This simplifies the sample and improves sensitivity. A preferred method of pre-fractionation involves contacting the biological sample with an anion exchange chromatographic material, such as Q HyperD (BioSepra, SA). The bound material is then subject to stepwise pH elution using buffers at pH 9, pH 7, pH 5 and pH 4. Various fractions containing the ApoA-II isoform biomarker are collected.

The biological sample to be tested (preferably pre-fractionated) can be contacted with an affinity capture probe comprising an cation exchange adsorbent (preferably a WCX ProteinChip array (Ciphergen Biosystems, Inc.)) or an IMAC adsorbent (preferably an IMAC3 ProteinChip array (Ciphergen Biosystems, Inc.)). The probe is washed with a buffer that will retain the biomarker while washing away unbound molecules. A suitable wash buffer for ApoA-II isoform biomarker is described in the Examples. The ApoA-II isoform biomarker may then be detected by laser desorption/ionization mass spectrometry.

Alternatively, antibodies that recognize an ApoA-II isoform biomarker can be attached to the surface of a probe, such as a pre-activated PS 10 or PS20 ProteinChip array (Ciphergen Biosystems, Inc.). These antibodies can capture the ApoA-11 isoform biomarker from a biological sample onto the probe surface. Then the ApoA-II isoform biomarker can be detected by, e.g., laser desorption/ionization mass spectrometry.

5.3. Detection by Immunoassay

In another embodiment, the ApoA-II isoform biomarkers of this invention can be detected by immunoassay. Immunoassay requires biospecific capture reagents, such as antibodies, to capture the ApoA-II isoform biomarkers. Furthermore, the assay may be designed to specifically distinguish ApoA-II isoform protein from ApoA-II as described by Gordon et al. (J. Biol Chem, 258:14054-14059, 1983) and Scanu et al. (Biochem Biophys Acta, 351:341-347, 1974). This can be done, for example, by employing a sandwich assay in which one antibody captures more than one form (e.g., an antibody recognizing and binding to ApoA-II and ApoA-II isoform) and second, distinctly labeled antibodies, specifically recognize and bind, and provide distinct detection of, the various forms (e.g., an antibody preferentially recognizing and binding to an ApoA-II isoform).

This invention contemplates various in vitro assays for the detection of an ApoA-II isoform polypeptide in a biological sample. Useful assays include enzyme linked immunosorbent assays (ELISAs; including sandwich ELISA and competitive ELISA), Western blots, immunoprecipitation, immunohistochemistry, immunofluorescence, radioimmune assay (RIA), and/or immunoradiometric assay (IRMA). These assays are well known in the art.

The ApoA-II isoform may be detected by using an antibody comprising a detectable label. A "labeled antibody" includes antibodies that are labeled by a detectable means and include enzymatically, radioactively, fluorescently, chemiluminescently, and/or bioluminescently labeled antibodies.

Enzymes which can be used to detectably label antibodies include, but are not limited to, horseradish peroxidase, malate dehydrogenase, staphylococcal nuclease, delta-5-steroid isomerase, yeast alcohol dehydrogenase, alpha-glycerophosphate dehydrogenase, triose phosphate isomerase, alkaline phosphatase, beta-galactosidase and glucose-6-phosphate dehydrogenase.

Particularly useful isotopes for radioactively labeling of antibodies include, but are not limited to $^{3}H$, $^{131}I$, $^{123}I$, $^{32}P$, $^{35}S$, $^{14}C$, $^{51}Cr$, $^{36}Cl$, $^{57}Co$, $^{58}Co$, and preferably $^{125}I$.

Among the most commonly used fluorescent labeling compounds are fluorescin isothiocyanate, rhodamine, phycoerytherin, phycocyanin, allophycocyanin, o-phtaldehyde and fluorescamine. Fluorescence-emitting metal atoms such as Eu (europium), and other lanthanides, can also be used.

Examples of particularly useful chemiluminescent labeling compounds are luminol, luciferin, isoluminol, aromatic acridinium ester, imidazole, acridinium salt and oxalate ester. Important bioluminescent compounds for the purpose of labeling antibodies are luciferin, luciferase and aequorin.

In addition, monoclonal antibodies of the present invention can be coupled to low molecular weight haptens. These haptens can then be specifically detected by means of a second reaction. For example, it is common to use such haptens as biotin, which reacts with avidin, or dinitrophenyl, pyridoxal and fluorescein, which can react with specific antihapten antibodies.

In the diagnostic and prognostic assays of the invention, the amount of binding of the antibody to the biological sample can be determined by the intensity of the signal emitted by the labeled antibody, and/or by the number of cells in the biological sample bound to the labeled antibody.

Following any of the above detection methods, the bound ApoA-II isoform may optionally be further analyzed by PAGE, column chromatography or any other method described herein to determine the molecular weight of the bound ApoA-II isoform.

Furthermore, in vivo techniques for detection of a an ApoA-II isoform polypeptide include introducing into a subject a labeled antibody directed against the ApoA-II isoform polypeptide. For example, the antibody can be labeled with a radioactive marker whose presence and location in a subject can be detected by standard imaging techniques.

5.4. Detection by PAGE

ApoA-II isoforms as described herein may be differentiated by their mass. In a preferred embodiment of the present invention, determining the amount of the bound ApoA-II isoform is done by polyacrylamide gel electrophoresis (PAGE) analysis. Analysis by PAGE may optionally be followed by Western blotting and detection of the ApoA-II isoform with an anti ApoA-II isoform antibody.

PAGE may be either one-dimensional (ID) or two-dimensional (2D). Two-dimensional PAGE has been the classical approach to explore the proteome for separation and detection of differences in protein expression (Srinivas et al., Clin Chem, 47:1901-1911, 2001; Adam et al., Proteomics 1:1264-1270, 2001). Further, advances in 2D-PAGE technology coupled with robotics and software programs for identifying potential protein alterations have improved this proteomic system.

5.5. Detection by HPLC

ApoA-II isoforms as described herein may be differentiated by their mass. In a preferred embodiment of the present invention, determining the amount of the bound ApoA-II isoform is done by detecting the ApoA-II isoforms by high-performance liquid chromatography (HPLC) as is known in the art. Briefly, HPLC, using a combination of separation techniques, can be used to separate molecules of biological samples at higher resolution. Extremely sharp peaks on the elution profile can be produced.

6. Determination of Subject Prostate Cancer Status

The present invention provides a method for determining prostate cancer status in a subject, the method comprising the steps of (a) providing a biological sample from the subject; (b) contacting the biological sample with a biospecific capture reagent capable of capturing an ApoA-II isoform, the ApoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15, whereby the ApoA-II isoform is bound to the biospecific capture reagent; (c) determining the amount of the bound ApoA-II isoform; and (d) correlating the amount of the bound ApoA-II isoform to prostate cancer status. Thus, the ApoA-II isoforms of the present invention may be used as a serum marker for detecting prostate cancer.

In another preferred embodiment of the present invention, a method for determining prostate cancer status in a subject is provided, the method comprising the steps of (a) providing a biological sample from the subject; (b) detecting or determining absence, presence or amount of an ApoA-II isoform, the APoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15; and (c) correlating the absence, presence or amount of the ApoA-II isoform to prostate cancer status. This method embraces the specifics outlined above.

In one embodiment of the present invention, the method comprises the step of comparing the amount of the ApoA-II isoform in the biological sample with the amount of an ApoA-II isoform in a biological sample from one or more subjects free from prostate cancer or with a previously determined reference range for an ApoA-II isoform in subjects free from prostate cancer.

6.1. Prostate Cancer versus Normal

In a preferred embodiment of the present invention, the prostate cancer status in a subject is prostate cancer versus normal, i.e., a determining a difference between prostate cancer subjects and normal or healthy subjects. Also encompassed by this invention is a method of diagnosing prostate cancer in a subject. In addition, this invention pertains to a method of diagnosing prostate cancer metastasis in a subject.

These methods comprise the steps of (a) providing a biological sample from the subject; (b) contacting the biological sample with a biospecific capture reagent capable of capturing an ApoA-II isoform, the ApoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15, whereby the ApoA-II isoform is bound to the biospecific capture reagent; (c) determining the amount of the bound ApoA-II isoform; and (d) correlating the amount of the bound ApoA-II isoform to prostate cancer status.

The amount of ApoA-II in normal (i.e., non-cancerous) biological samples can be assessed in a variety of ways as described herein. In one embodiment, this normal amount of expression is determined by assessing the level of ApoA-II isoform in prostate cells which appear to be non-cancerous and by comparing this normal amount with the amount of ApoA-II in prostate cells which is suspected of being cancerous and/or metastatic. Alternatively, the 'normal' amount of ApoA-II isoform expression may e determined by assessing the amount of ApoA-II isoform in one or more samples obtained from one or more non-cancer-afflicted individuals.

Using the methods of the invention, ApoA-II isoform levels are determined in a biological sample from a subject suspected of having prostate cancer and in one or more comparable biological samples from normal or healthy subjects. An ApoA-II isoform level detected in a biological sample from a subject suspected of having prostate cancer that is higher than the ApoA-II isoform level detected in a comparable biological sample from a normal or healthy subject, indicates that the subject suspected of having prostate cancer has or is likely to have prostate cancer.

6.2. Prostate Cancer versus Benign Prostatic Hyperplasia

In another preferred embodiment of the present invention, the prostate cancer status in a subject is prostate cancer versus benign prostate hyperplasia (BPH), i.e., a determining a difference between prostate cancer subjects and subjects having benign prostate hyperplasia.

With BPH, PSA levels rise in proportion to prostate size. In the majority of cases, PSA elevation is due to BPH or prostatitis rather than carcinoma. However, often, a proper diagnosis of prostate cancer is obscured because of these high PSA levels. Thus, when PSA levels are usually in the range of 4-10 ng/ml the PSA test seems to lack specificity to distinguish between benign prostatic hyperplasia and prostate cancer without additional tests, such as digital rectal exam and/or prostate needle biopsy (McCormack et al., Urology, 45:729-744, 1995).

Using the methods of the invention, ApoA-II isoform levels are determined in a biological sample from a subject suspected of having prostate cancer and in one or more comparable biological samples from subjects having benign prostatic hyperplasia. An ApoA-II isoform level detected in a biological sample from a subject suspected of having prostate cancer that is higher than the ApoA-II isoform level detected in a comparable biological sample from subjects having benign prostatic hyperplasia, indicates that the subject suspected of having prostate cancer has or is likely to have prostate cancer.

6.3. Prostate Cancer versus Non-Prostate Cancers

In a preferred embodiment of the present invention, the prostate cancer status in a subject is prostate cancer versus non-prostate cancer, i.e., a discriminating between prostate cancer subjects and subjects having cancer other than prostate cancer based on the detection of ApoA-II isoform levels in prostate cancer subjects and ApoA-II isoform levels in non-prostate cancer subjects.

Figure 7:
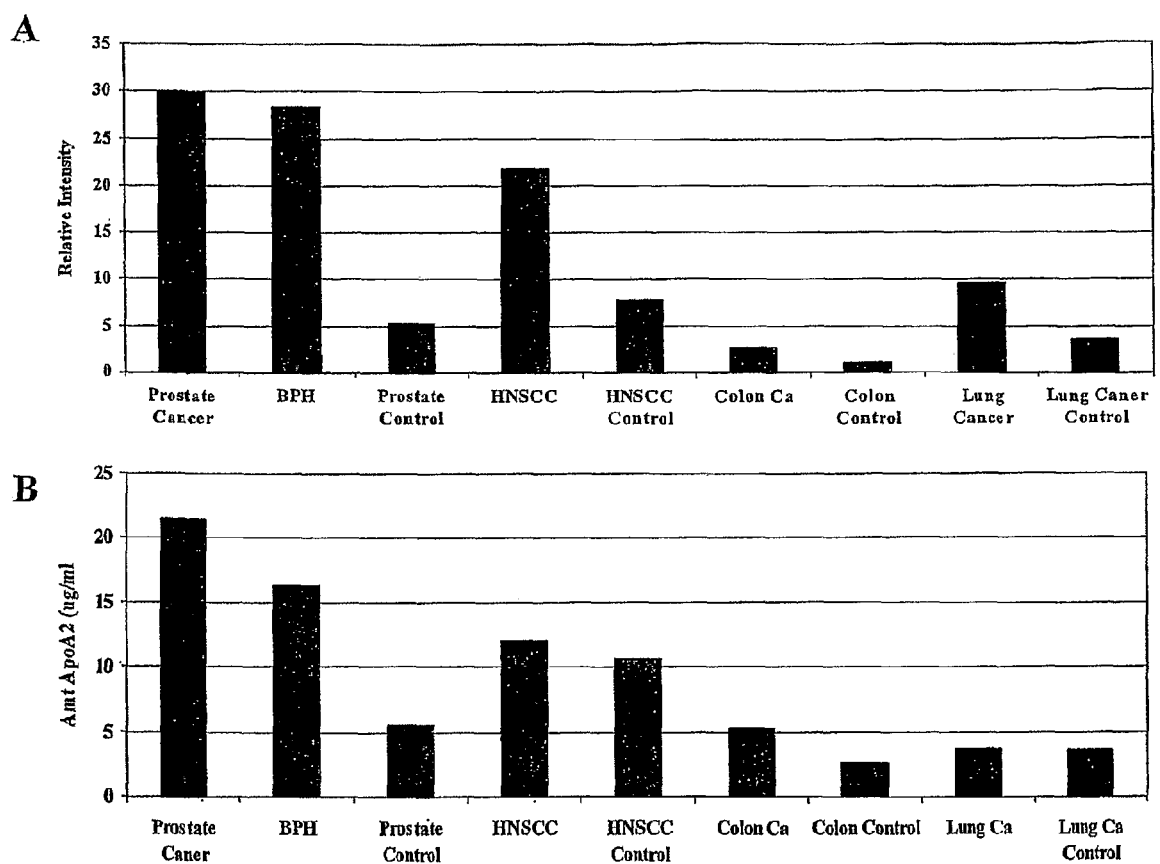
FIG. 7 shows a comparative ApoA-II isoform SELDI-immunoassay. Using the SELDI-based immunoassay, levels of ApoA-II isoform were tested in cancer and control serum samples of Prostate (7 cancers, 7 BPH and 4 controls), Head and Neck. Squamous Cell Carcinoma or HNSCC (6 cancers and 4 controls), Colon (10 cancers and 4 controls) and Lung (8 cancer and 4 controls). (A) Relative normalized intensity of the 8.9K m/z peak on IMAC-$Cu^{2+}$ ProteinChips®. (B) Relative amount of serum levels of ApoA-II isoform as observed in the SELDI-based immunoassay. Amount of ApoA-II isoform (μg/ml) is calculated using the values obtained in the titration of purified ApoA-II isoform.

An ApoA-II isoform of this invention is particularly useful to discriminate between prostate cancer and other common non prostate cancers, such as head and squamous cell carcinoma (HNSCC), colon cancer and lung cancer (FIG. 7). Typically, ApoA-III isoform is not present at elevated levels in those non-prostate cancers or the ApoA-II isoform levels in those non-prostate cancers is significantly lower than the ApoA-II isoform level found in prostate cancer.

6.4. Screening Diagnosis or Prognosis of Prostate Cancer in a Subject

In another preferred embodiment of the present invention, the prostate cancer status in a subject is determined as part of screening, diagnosis or prognosis of prostate cancer in the subject.

Using the methods of the invention, ApoA-II isoform levels are determined in a biological sample from a subject suspected to be screened for prostate cancer. An ApoA-II isoform level detected in a biological sample from a subject to be screened for prostate cancer that is higher than the ApoA-II isoform level detected in a comparable biological sample from normal or healthy subjects or higher than a predetermined base level, indicates that the subject screened for prostate cancer has or is likely to have prostate cancer.

6.5. Determining Susceptibility of a Subject to Prostate Cancer

In another preferred embodiment of the present invention, the prostate cancer status is determined as part of determining susceptibility of the subject to prostate cancer.

Using the methods of the invention, ApoA-II isoform levels are determined in a biological sample from a subject suspected to be susceptible to prostate cancer. An ApoA-II isoform level detected in a biological sample from a subject suspected to be susceptible to prostate cancer that is higher than the ApoA-II isoform level detected in a comparable biological sample from normal or healthy subjects or higher than a predetermined base level, indicates that the subject suspected to be susceptible to prostate cancer has or is likely to have prostate cancer.

6.6. Identifying a Risk for a Subject of Developing Prostate Cancer

In a preferred embodiment of this invention the prostate cancer status is determined as part of identifying a risk for the subject of developing prostate cancer. In another embodiment the prostate cancer status is determined as part of identifying a risk for the subject of prostate cancer recurrence.

Amounts of ApoA-II isoform biomarker or patterns are characteristic of various prostate cancer risk states, e.g., high, medium or low. The risk of developing prostate cancer may be determined by measuring the ApoA-II isoform biomarker or biomarkers and then either submitting them to a classification algorithm or comparing them with a reference amount and/or pattern of ApoA-II isoform biomarkers that is associated with the particular risk level.

Using the methods of the invention, ApoA-II isoform levels are determined in a biological sample from a subject for whom a risk of developing prostate cancer is to be determined. An ApoA-II isoform level detected in a biological sample from a subject for whom a risk of developing prostate cancer is to be determined that is higher than the ApoA-II isoform level detected in a comparable biological sample from normal or healthy subjects or higher than a predeter-

6.7. Determining Stage or Severity of Prostate Cancer

In one embodiment, this invention provides methods for determining the stage or severity of prostate cancer in a subject. The stage or severity of prostate cancer refers to different clinical stages of the tumor. Clinical stages of tumor are defined by various parameters which are well-established in the field of medicine. Some of the parameters include morphology, size of tumor, the degree in which the tumor has metastasized through a patient's body and the like. Prostate cancers can be classified or staged based on their aggressiveness. There are several different ways to stage prostate cancer (Zagars et al., Cancer 73:1904-1912, 1994).

Prostate cancer (PCA) stages are commonly evaluated according to a scale divided as A, B, C and D (Whitmore-Jewett system). Tumors in stage A are microscopic; stage Al designates tumors confined to a relatively small area and composed of well-differentiated tissue; stage $A_2$ tumors are more diffuse and less well differentiated; stage B tumors are large enough to be felt during a rectal examination; and stage C prostate cancers have spread throughout the gland and typically have pushed past the borders of the prostate into surrounding structures. Stage D tumors have metastasized, e.g., to lymph nodes, bone, or other organs.

Alternatively, tumors are also staged by the TNM staging system, in which tumors are ranked on a scale of progressively worsening disease from T1a to T4b (e.g., T1c tumors are non-palpable and non-visible that were detected by elevated blood levels of prostate specific antigen). The TNM system for staging prostate cancer is summarized in Table 1, which follows. Of tumors characterized as being in stages $A_2$, B, or C, 25% to 50% turn out, on further testing, to be metastatic. Methods involving procedures for removal or destruction of prostatic tumor tissue usually are employed with non-metastasized cancers. For example, radical prostatectomy preferably is used with stage A, B and some stage C tumors (i.e., where the tumor growth has not extended considerably beyond the borders of the prostate gland) as well as stage T1c tumors. X-ray therapy (e.g., external or interstitial) preferably is used with stage A, B or C tumors as well as T1c tumors. Additional diagnostic tools might aid in distinguishing cases suitable for various treatments.

TABLE 1

The TNM System of Prostate Tumor Classification

| | |
|---|---|
| TX | Primary tumor cannot be assessed |
| T0 | No evidence of primary tumor |
| T1 | Clinically unapparent tumor, not palpable nor visible by imaging |
| T1a | Tumor and incidental histological finding in 5% or less of tissues resected |
| T1b | Tumor and incidental histological finding in more than 5% of tissues resected |
| T1c | Tumor identified by needle biopsy (e.g., because of elevated serum PSA levels) |
| T2 | Tumor confined within the prostate (Note: Tumor found in one or both lobes by needle biopsy, not palpable or visible by imaging, is classified as T1c) |
| T2a | Tumor involves half of a lobe or less |
| T2b | Tumor involves more than half a lobe but not both lobes |
| T2c | Tumor involves both lobes |
| T3 | Tumor extends through the prostate capsule (Note: Invasion into the Prostatic apex or into (but not beyond) the Prostatic capsule is classified as T2) |
| T3a | Unilateral extracapsular extension |
| T3b | Bilateral extracapsular extension |
| T3c | Tumor invades seminal vesicle(s) |
| T4 | Tumor is fixed or invades adjacent structures other than seminal vesicles |
| T4a | Tumor invades bladder neck and/or external sphincter and/or rectum |
| T4b | Tumor invades levator muscles and/or is fixed to pelvic wall. |

Another commonly used system for determining the prognosis of a patient with prostate cancer is the Gleason scoring system. The "Gleason score" or "Gleason grade" is a value from 1 (well differentiated) to 5 (poorly differentiated) based on the examination of slices of prostate cancer tissue under a microscope. The lower the Gleason score the more the prostate cancer tissue resembles the structure of normal prostate tissue and the less aggressive the cancer is likely to be.

The "combined Gleason score" or "Gleason sum" is a value from 2 (least anaplastic) to 10 (most anaplastic) based on the Gleason scores of the 2 most common 10 histological patterns in the prostate cancer tissue. The lower the Gleason sum, the better the prognosis for the patient. The most common Gleason sums are 6 and 7, which often represent a gray zone for cancer prognosis. Tables 2A through 2D (the Partin Coefficient Tables), which follow, show the probability of organ-confined prostate cancer based on the PSA levels, Gleason score, and stage of the prostate cancer.

TABLE 2A

Prediction of Probability of Organ-Confined Disease (for PSA = 0.0-4.0 ng/ml)

| Gleason Score | Stage T1a | Stage T1b | Stage T1c | Stage T2a | Stage T2b | Stage T2c | Stage T3a |
|---|---|---|---|---|---|---|---|
| 2-4 | 90 | 80 | 89 | 81 | 72 | 77 | ... |
| 5 | 82 | 66 | 81 | 68 | 57 | 62 | 40 |
| 6 | 78 | 61 | 78 | 64 | 52 | 57 | 35 |
| 7 | ... | 43 | 63 | 47 | 34 | 38 | 19 |
| 8-10 | ... | 31 | 52 | 36 | 24 | 27 | ... |

TABLE 2B

Prediction of Probability of Organ-Confined Disease
(for PSA = 4.1-10.0 ng/ml)

| Gleason Score | Stage T1a | Stage T1b | Stage T1c | Stage T2a | Stage T2b | Stage T2c | Stage T3a |
|---|---|---|---|---|---|---|---|
| 2-4 | 84 | 70 | 83 | 71 | 61 | 66 | 43 |
| 5 | 72 | 53 | 71 | 55 | 43 | 49 | 27 |
| 6 | 67 | 47 | 67 | 51 | 38 | 43 | 23 |
| 7 | 49 | 29 | 49 | 33 | 22 | 25 | 11 |
| 8-10 | 35 | 18 | 37 | 23 | 14 | 15 | 6 |

TABLE 2C

Prediction of Probability of Organ-Confined Disease
(for PSA = 10.1-20.0 ng/ml)

| Gleason Score | Stage T1a | Stage T1b | Stage T1c | Stage T2a | Stage T2b | Stage T2c | Stage T3a |
|---|---|---|---|---|---|---|---|
| 2-4 | 76 | 58 | 75 | 60 | 48 | 53 | ... |
| 5 | 61 | 40 | 60 | 43 | 32 | 36 | 18 |
| 6 | ... | 33 | 55 | 38 | 26 | 31 | 14 |
| 7 | 33 | 17 | 35 | 22 | 13 | 15 | 6 |
| 8-10 | ... | 9 | 23 | 14 | 7 | 8 | 3 |

TABLE 2D

Prediction of Probability of Organ-Confined Disease
(for PSA > 20 ng/ml)

| Gleason Score | Stage T1a | Stage T1b | Stage T1c | Stage T2a | Stage T2b | Stage T2c | Stage T3a |
|---|---|---|---|---|---|---|---|
| 2-4 | ... | 38 | 58 | 41 | 29 | ... | ... |
| 5 | ... | 23 | 40 | 26 | 17 | 19 | 8 |
| 6 | ... | 17 | 35 | 22 | 13 | 15 | 6 |
| 7 | ... | ... | 18 | 10 | 5 | 6 | 2 |
| 8-10 | ... | 3 | 10 | 5 | 3 | 3 | 1 |

Numbers in Tables 2A, 2B, 2C and 2D represent percent predictive probabilities (95% confidence interval); ellipses indicate lack of sufficient data to calculate probability.

Each stage of the prostate cancer as described herein has a characteristic amount of ApoA-II isoform. The stage of prostate cancer is determined by measuring the ApoA-II isoform and then either submitting it to a classification algorithm or comparing it with a reference amount and/or pattern of ApoA-II isoform that is associated with the particular prostate cancer stage or severity as described herein.

6.8. Determining the Course of Prostate Cancer (Progression, Regression)

In one preferred embodiment of the present invention, the prostate cancer status is determined as part of determining the course of prostate cancer. Thus, the invention provides methods for determining the course of disease, particularly prostate cancer, in a subject. Disease course refers to changes in disease status over time, including disease progression (worsening) and prostate cancer regression (improvement). Regression includes tumor remission, reduction or diminution in tumor size, decrease in number cancerous cells, and lessening of symptoms associated with prostate cancer. Over time, the amounts or relative amounts (e.g., the pattern) of the ApoA-II isoform changes.

Using the methods of the invention, ApoA-II isoform levels are determined in a biological sample from a subject at various times. An ApoA-II isoform level detected in a biological sample from a subject at a first time (t1) that is higher than the ApoA-II isoform level detected in a comparable biological sample from the same subject taken at a second time (t2), indicates that the course of prostate cancer in the subject is regressing. Likewise, a higher ApoA-II isoform level at a second time compared to an ApoA-II isoform level at a first time, indicates that the course of prostate cancer in the subject is progressing.

ApoA-II isoform biomarker may increase upon progression of prostate cancer, while another biomarker, X, may decrease. Therefore, the trend of these biomarkers, either increased or decreased over time toward prostate cancer or non-prostate cancer indicates the course of prostate cancer.

In another embodiment, this method involves measuring one or more biomarkers, one of which is an ApoA-II isoform, in a subject at least at two different time points, e.g., a first time and a second time, and comparing the change in amounts, if any. The course of disease is determined based on these comparisons.

6.9. Monitoring the Effect of an Anti-Prostate Cancer Drug or a Therapy Administered to a Subject with Prostate Cancer In a preferred embodiment of the present invention, the prostate cancer status is determined as part of monitoring the effect of an anti-prostate cancer drug or a therapy administered to the subject diagnosed with prostate cancer. The effect of an anti-prostate cancer drug or a therapy administered to a subject with prostate cancer may include progression of prostate cancer (worsening) and prostate cancer regression (improvement).

Using the methods of the invention, ApoA-II isoform levels are determined in a biological sample from a subject at various times of having been given an anti-prostate cancer drug or a therapy. An ApoA-II isoform level detected in a biological sample from a subject at a first time (t1; e.g., before giving an anti-prostate cancer drug or a therapy) that is higher than the ApoA-II isoform level detected in a comparable biological sample from the same subject taken at a second time (t2; e.g., after giving an anti-prostate cancer drug or a therapy), indicates that the prostate cancer in the subject is regressing. Likewise, a higher ApoA-II isoform level at a second time compared to an ApoA-II isoform level at a first time, indicates that the prostate cancer in the subject is progressing.

ApoA-II isoform biomarker may decrease upon giving an anti prostate cancer drug or a therapy to a subject with prostate cancer, while another biomarker, X, may increase. Therefore, the trend of these biomarkers, either increased or decreased over time toward prostate cancer or non-prostate cancer indicates the effect of an anti prostate cancer drug or therapy administered to a subject diagnosed with prostate cancer.

In another embodiment, this method involves measuring one or more biomarkers, one of which is an ApoA-II isoform, in a subject at least at two different time points, e.g., a first time and a second time, and comparing the change in amounts, if any. The effect of the anti-prostate cancer drug or therapy on the progression or regression of prostate cancer is determined based on these comparisons. Thus, this method is useful for determining the response to treatment. If a treatment is effective, then the ApoA-II isoform biomarker will trend toward normal, while if treatment is ineffective, the ApoA-II isoform biomarker will trend toward disease indications.

6.10. Single Markers

An ApoA-II isoform biomarker of the invention can be used in diagnostic tests to assess prostate cancer status in a subject, e.g., to diagnose prostate cancer.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of actual positives who test as positive. Negative predictive value is the percentage of actual negatives that test as negative.

An ApoA-II isoform biomarker of this invention shows a statistical difference in different prostate cancer statuses of at least $p \leq 0.05$, $p \leq 10^{-2}$, $p \leq 10^{-3}$, $p \leq 10^4$ or $p \leq 10^{-5}$. Diagnostic tests that use an ApoA-II isoform biomarker alone or in combination show a sensitivity and specificity of at least 75%, at least 80%, at least 85%, at least 90%, at least 95%, at least 98% and about 100%.

An ApoA-II isoform biomarker is differentially present in prostate cancer, and, therefore, each is individually useful in aiding in the determination of prostate cancer status. A method of the present invention involves, first, measuring the selected biomarker in a biological sample of a subject using the methods described herein, e.g., capture an ApoA-II isoform on a SELDI biochip followed by detection by mass spectrometry and, second, comparing the measurement with a diagnostic amount or cut-off that distinguishes a positive prostate cancer status (e.g., prostate cancer) from a negative prostate cancer status (e.g., normal or healthy). The diagnostic amount represents a measured amount of an ApoA-II isoform biomarker above which or below which a subject is classified as having a particular prostate cancer status. For example, if the ApoA-II isoform biomarker is up-regulated compared to normal during prostate cancer, then a measured amount above the diagnostic cutoff provides a diagnosis of prostate cancer. Alternatively, if the ApoA-II isoform biomarker is down-regulated during prostate cancer, then a measured amount below the diagnostic cutoff provides a diagnosis of prostate cancer. As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the ApoA-II isoform biomarker in a statistically significant number of samples from subjects with the different prostate cancer statuses, as was done here, and drawing the cut-off to suit the diagnostician's desired levels of specificity and sensitivity.

6.11. Combinations of Markers

While individual biomarkers are useful diagnostic biomarkers, it has been found that a combination of biomarkers can provide greater predictive value of a particular status than single biomarkers alone. Specifically, the detection of a plurality of biomarkers in a sample can increase the sensitivity and/or specificity of the test.

In one form of the invention, methods for determining prostate cancer status in a subject comprises detecting at least two protein biomarkers in a biological sample from the subject. One of the at least two protein biomarkers comprises an ApoA-II isoform of the present invention. The other of the at least two protein biomarkers comprises a prostate cancer-specific biomarker X wherein the prostate cancer-specific biomarker X is different from the ApoA-II isoform. Thus, in one embodiment of the present invention, the method for determining prostate cancer status in a subject comprises the step of (e) contacting the biological sample with a biospecific capture reagent capable of capturing a prostate cancer-specific biomarker X, wherein the prostate cancer-specific biomarker X is different from the ApoA-II isoform. The absence, presence or amount of prostate cancer-specific biomarker X may be determined as described herein.

Prostate cancer-specific biomarkers X that are useful for the present invention include, but are not limited to, PSA, novel forms of PSA (U.S. Patent Application Pub. No. 2003/0119033 A1, incorporated herein by reference in its entirety), Pin1 (U.S. Patent Application Pub. No. 2003/0073096 A1, incorporated herein by reference in its entirety), IAP (U.S. Patent Application Pub. No. 2003/0224399 A1, incorporated herein by reference in its entirety), PSMA (U.S. Patent Application Pub. No. 2004/0018519 A1, incorporated herein by reference in its entirety) or any of the prostate cancer-specific biomarkers identified in WO 2004/030511 A2 and in WO 03091695 (incorporated herein by reference in their entireties).

6.12. Subject Management

6.12.1. Managing Subject Treatment

In certain embodiments of the methods of determining prostate cancer status, the methods further comprise managing subject treatment based on the status. Such management includes the actions of the physician or clinician subsequent to determining prostate cancer status. For example, if a physician makes a diagnosis of prostate cancer, then a certain regime of treatment, such as prescription or administration of an anti-prostate cancer drug or therapy or surgery might follow. Alternatively, a diagnosis of prostate cancer, BPH or non-prostate cancer might be followed with further testing to determine a specific disease that might the patient might be suffering from. Also, if the diagnostic test gives an inconclusive result on prostate cancer status, further tests may be called for. These tests may include rectal examination, transrectal ultrasonography (TRUS) or magnetic resonance imaging (MRI), bone scanning, X-rays, skeletal muscle survey, intravenous pyelography, CAT-scan, and biopsy (reviewed in Garnick, Annals of Internal Medicine, 118:803-818, 1993; Garnick, Scientific American 270:72-81, 1994).

6.12.2. Communication of Result to Subject

Additional embodiments of the invention relate to the communication of prostate cancer status or assay results or diagnoses to technicians, physicians or patients, for example. In certain embodiments, computers will be used to communicate prostate cancer status, assay results or diagnoses to interested parties, e.g., physicians and their patients. In some embodiments, the assays will be performed or the assay results analyzed in a country or jurisdiction which differs from the country or jurisdiction to which the prostate cancer status, results or diagnoses are communicated.

The present invention provides a method comprising the step of (a) communicating to a subject a diagnosis relating to prostate cancer status determined from the correlation of an ApoA-II isoform in a sample from the subject, the ApoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15. The diagnosis may be communicated to the subject via a computer-generated medium.

In a preferred embodiment of the invention, a prostate cancer status or diagnosis based on the presence, absence or amount in a test subject of an ApoA-II isoform biomarker is communicated to the subject as soon as possible after the prostate cancer status or diagnosis is obtained. The prostate cancer status or diagnosis may be communicated to the subject by the subject's treating physician. Alternatively, the prostate cancer status or diagnosis may be sent to a test subject by email or communicated to the subject by phone. A computer may be used to communicate the prostate cancer status diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761 (incorporated herein by reference in its entirety); however, the present invention is not limited to methods which utilize this particular communications system. In certain embodiments of the methods of the invention, all or some of the method steps, including the assaying of samples, diagnosing of diseases, and communicating of assay results, prostate cancer status or diagnoses, may be carried out in diverse (e.g., foreign) jurisdictions.

7. Generation of Classification Algorithms for Determining Prostate Cancer Status It is another object of the present invention to provide software for classifying, determining, or qualifying a prostate cancer status.

In one embodiment of the present invention, the software comprises (a) a code that accesses data attributed to a biological sample, the date comprising measurement of an ApoA-II isoform, the ApoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15; and (b) a code that executes a classification algorithm that classifies the prostate cancer status of the biological sample as a function of the measurement.

In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased; prostate cancer versus non-prostate cancer).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT Internatl. Publ. No. WO 01/31580 (Barnhill et al., "Methods and devices for identifying patterns in biological systems and methods of use thereof"), U.S. Patent Application No. 2002 0193950 A1 (Gavin et al., "Method or analyzing mass spectra"), U.S. Patent Application No. 2003 0004402 A1 (Hitt et al., "Process for discriminating between biological states based on hidden patterns from biological data"), and U.S. Patent Application No. 2003 0055615 A1 (Zhang and Zhang, "Systems and methods for processing biological expression data"), all of which are incorporated herein by reference in their entireties.

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers for Prostate Cancer. The classification algorithms, in turn, form the base for diagnostic tests by providing diagnostic values (e.g., cut-off points) for biomarkers used singly or in combination.

8. Kits for Determining Prostate Cancer Status

In another aspect, the present invention provides kits for determining prostate cancer status, wherein the kits are used to detect ApoA-II isoform biomarkers according to the invention.

In one embodiment of the present invention a kit for determining prostate cancer status is provided, the kit comprising (a) a solid support comprising at least one biospecific capture reagent attached thereto, wherein the biospecific capture reagent is capable of capturing an ApoA-II isoform, the ApoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15; and (b) instructions for using the solid support to detect the ApoA-II isoform. In a preferred embodiment, the solid support is a SELDI probe. The kit may further comprise (c) a container containing the ApoA-II isoform.

In another preferred embodiment the kits of this invention comprise a biospecific capture reagent capable of capturing a prostate cancer-specific biomarker X, wherein the prostate cancer-specific biomarker X is different from the ApoA-II isoform. Useful prostate cancer-specific biomarkers X are described herein.

In another embodiment of the present invention a kit for determining prostate cancer status is provided, the kit comprising (a) a solid support comprising at least one biospecific capture reagent attached thereto, wherein the biospecific capture reagent is capable of capturing an ApoA-II isoform, the ApoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15; and (b) a container containing the ApoA-II isoform. The solid support comprising the biospecific capture reagent may be a SELDI probe, a chip, a microtiter plate, a bead or a resin.

In yet another embodiment of the present invention, a kit for determining prostate cancer status is provided, the kit comprising (a) an antibody capable of binding to an ApoA-II isoform, the ApoA-II isoform comprising (i) the amino acid sequence VKSPELQAEAK (SEQ ID NO: 1) and (ii) the amino acid sequence SKEQLTPLIK (SEQ ID NO:2) and wherein the ApoA-II isoform has a molecular weight of about 8943 Dalton +/−15; (b) reagents for PAGE and Western blotting; and (c) instructions for using the antibody to detect the ApoA-II isoform.

In one embodiment, the kit comprises a solid support, such as a chip, a microtiter plate or a bead or resin having a capture reagent attached thereon, wherein the capture reagent binds an ApoA-II isoform biomarker of the invention. Thus, for example, the kits of the present invention can comprise mass spectrometry probes for SELDI, such as ProteinChip® arrays. In the case of biospecific capture reagents, the kit can comprise a solid support with a reactive surface, and a container comprising the biospecific capture reagent.

Thus, for example, the kits of this invention could include a solid support having a hydrophobic function, such as a protein biochip (e.g., a Ciphergen H50 ProteinChip array, e.g., ProteinChip array) and a sodium acetate buffer for washing the solid support as well as instructions providing a protocol to measure the ApoA-II isoform biomarkers of this invention on the chip and to use these measurements to diagnose prostate cancer status.

The kit can also comprise a washing solution or instructions for making a washing solution, in which the combination of the biospecific capture reagent and the washing solution allows capture of the ApoA-II isoform biomarker or biomarkers on the solid support for subsequent detection by, e.g., mass spectrometry. The kit may include more than one type of adsorbent, each present on a different solid support.

In a further embodiment, such a kit can comprise instructions for suitable operational parameters in the form of a label or separate insert. For example, the instructions may inform a consumer about how to collect a biological sample, how to wash the probe or the particular ApoA-II isoform biomarkers to be detected.

In yet another embodiment, the kit can comprise one or more containers with ApoA-II isoform biomarker samples, to be used as standard(s) for calibration.

9. Use of ApoA-II Isoform for Prostate Cancer in Screening Assays and Methods of Treating Prostate Cancer The methods of the present invention have other applications as well. For example, the ApoA-II isoform biomarkers can be used to screen for compounds that modulate the expression of the ApoA-II isoform biomarkers in vitro or in vivo, which compounds in turn may be useful in treating or preventing prostate cancer in patients. In another example, the ApoA-II isoform biomarkers can be used to monitor the response to treatments for prostate cancer. In yet another example, the ApoA-II isoform biomarkers can be used in heredity studies to determine if the subject is at risk for developing prostate cancer.

Compounds suitable for therapeutic testing may be screened initially by identifying compounds which interact with an ApoA-II isoform biomarker. By way of example, screening might include recombinantly expressing an ApoA-II isoform biomarker, purifying the ApoA-II isoform biomarker, and affixing the ApoA-II isoform biomarker to a substrate or support. Test compounds would then be contacted with the substrate or support, typically in aqueous conditions, and interactions between the test compound and the ApoA-II isoform biomarker are measured, for example, by measuring elution rates as a function of salt concentration. Certain proteins may recognize and cleave an ApoA-II isoform biomarker, in which case the proteins may be detected by monitoring the digestion of an ApoA-II isoform biomarker in a standard assay, e.g., by gel electrophoresis of the proteins.

In a related embodiment, the ability of a test compound to inhibit the activity of an ApoA-II isoform biomarker may be measured. One of skill in the art will recognize that the techniques used to measure the activity of a particular biomarker will vary depending on the function and properties of the biomarker, such as the ApoA-II isoform biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of one of the biomarkers of this invention may also be measured. For example, the self-assembly of a multi-protein complex which includes one of the biomarkers of this invention may be monitored by spectroscopy in the presence or absence of a test compound. Alternatively, if the biomarker is a non-enzymatic enhancer of transcription factor, test compounds which interfere with the ability of the biomarker to enhance transcription may be identified by measuring the levels of biomarker-dependent transcription in vivo or in vitro in the presence and absence of the test compound.

Test compounds capable of modulating the activity of an ApoA-II isoform biomarker of this invention may be administered to patients who are suffering from or are at risk of developing prostate cancer or other cancer. For example, the administration of a test compound which increases the activity of a particular ApoA-II isoform biomarker may decrease the risk of prostate cancer in a patient if the activity of an ApoA-II isoform biomarker in vivo prevents the accumulation of proteins for prostate cancer. Conversely, the administration of a test compound which decreases the activity of an ApoA-II isoform biomarker may decrease the risk of prostate cancer in a patient if the increased activity of the ApoA-II isoform biomarker is responsible, at least in part, for the onset of prostate cancer.

In an additional aspect, the invention provides a method for identifying compounds useful for the treatment of disorders such as prostate cancer which are associated with increased levels of ApoA-II isoform. For example, in one embodiment, cell extracts or expression libraries may be screened for compounds which catalyze the cleavage of an ApoA-II isoform to form truncated forms of the ApoA-II isoform. In one embodiment of such a screening assay, cleavage of ApoA-II isoform may be detected by attaching a fluorophore to ApoA-II isoform which remains quenched when ApoA-II isoform is uncleaved but which fluoresces when the ApoA-II isoform is cleaved. Alternatively, a version of full-length ApoA-II isoform modified so as to render the amide bond between amino acids x and y uncleavable may be used to selectively bind or "trap" the cellular protesase which cleaves full-length ApoA-II isoform at that site in vivo. Methods for screening and identifying proteases and their targets are well-documented in the scientific literature, e.g., in Lopez-Ottin et al. (Nature Reviews, 3:509-519, 2002).

In yet another embodiment, the invention provides a method for treating or reducing the progression or likelihood of a disease, e.g., prostate cancer, which is associated with the increased levels of truncated ApoA-II isoform. For example, after one or more proteins have been identified which cleave full-length ApoA-II isoform, combinatorial libraries may be screened for compounds which inhibit the cleavage activity of the identified proteins. Methods of screening chemical libraries for such compounds are well-known in art. See, e.g., Lopez-Otin et al. (Nature Reviews, 3:509-519, 2002). Alternatively, inhibitory compounds may be intelligently designed based on the structure of ApoA-II isoform.

At the clinical level, screening a test compound includes obtaining biological samples from test subjects before and after the subjects have been exposed to a test compound. The levels in the biological samples of one or more of the ApoA-II isoform biomarkers of the present invention may be measured and analyzed to determine whether the levels of the ApoA-II isoform biomarkers change after exposure to a test compound. The samples may be analyzed by mass spectrometry, as described herein, or the samples may be analyzed by any appropriate means known to one of skill in the art. For example, the levels of one or more of the ApoA-II isoform biomarkers of this invention may be measured directly by Western blot using radio- or fluorescently-labeled antibodies which specifically bind to the ApoA-II isoform biomarkers.

Alternatively, changes in the levels of mRNA encoding the ApoA-II isoform biomarkers of this invention may be measured and correlated with the administration of a given test compound to a subject. In a further embodiment, the changes in the level of expression of one or more of the ApoA-II isoform biomarkers may be measured using in vitro methods and materials. For example, human tissue cultured cells which express, or are capable of expressing, one or more of the ApoA-II isoform biomarkers of this invention may be contacted with test compounds. Subjects who have been treated with test compounds will be routinely examined for any physiological effects which may result from the treatment. In particular, the test compounds will be evaluated for their ability to decrease prostate cancer likelihood in a subject. Alternatively, if the test compounds are administered to subjects who have previously been diagnosed with prostate cancer, test compounds will be screened for their ability to slow or stop the progression of prostate cancer.

Although the forgoing invention has been described in some detail by way of illustration and example for clarity and understanding, it will be readily apparent to one ordinary skill in the art in light of the teachings of this invention that certain variations, changes, modifications and substitution of equivalents may be made thereto without necessarily departing from the spirit and scope of this invention. As a result, the embodiments described herein are subject to various modifications, changes and the like, with the scope of this invention being determined solely by reference to the claims appended hereto.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The invention is further illustrated by the following examples, which are only illustrative and are not intended to limit the definition and scope of the invention in any way.

10. EXAMPLES

10.1 Example 1

Material and Methods 10.1.1. Serum Samples

Serum samples were obtained from the Virginia Prostate Center Tissue and Body Fluid Bank. Blood samples collected under the same protocols from properly consented patients diagnosed with either biopsy proven prostate cancer (PCa) or benign disease (BPH; PSA 4-10 ng/ml with multiple negative biopsies) were obtained from the Department of Urology, Eastern Virginia Medical School (EVMS), and the samples of healthy men cohort (NO; PSA<4.0 ng/ml with no evidence of prostate disease) were obtained from free screening clinics open to the general public. Only pretreatment samples obtained at the time of diagnosis of PCa or BPH were used for this study. Another group of serum samples from patients with cancers of the head and neck, colon and lung were utilized for comparative studies. Serum samples from head and neck cancer patients and controls were kindly provided by Dr. Brendan Stack at the Penn State College of Medicine, Hershey, Pa. Colon cancer and control serum samples were kindly provided by Drs. W. Bigbee and R. Schoen at the University of Pittsburgh Cancer Institute, Pittsburgh, Pa. and were obtained from individuals diagnosed with pre-treatment colorectal carcinoma or determined to be disease-free following endoscopy screening. Samples of Lung cancer and control sera were provided by Dr. William Rom at the New York University School of Medicine, Department of Environmental Medicine, New York, N.Y. All samples were obtained from properly consented patients through the institutional review board approved protocols.

10.1.2. Protein Purification

The accurate mass and chemical affinity of the protein of interest was established based on the SELDI profile and the ProteinChip® type and this information formed the basis for designing the two-dimensional purification process. Whole unfractionated serum samples from verified over-expressing and under-expressing samples were subjected to affinity and reverse-phase chromatography in parallel. Isolated fractions were then separated by mass through single dimension SDS-PAGE and silver stained for visualization of protein bands.

a) Metal-Affinity Chromatography

To complement the chip chemistry used for SELDI profiling (IMAC3-$Cu^{2+}$), whole serum was subjected to IMAC HyperCel® filtration (Ciphergen Biosystems Inc., Fremont, Calif.) as per the manufacturer's instructions on a Biomek® 2000 Automated Laboratory Workstation (Beckman Coulter Inc., Fullerton, Calif.). Briefly, IMAC (immobilized metal affinity capture) resin was regenerated with HPLC water for 30 min. After washing the resin thoroughly with water, the resin was charged with 0.1 M $CuSO_4$ for 30 min. Resin was then washed thoroughly with HPLC water followed by PBS. Twenty microliters of serum were processed in urea as described previously (Adam et al., Cancer Res, 62:3609-3614, 2002) and incubated with the resin for 40 min. After collecting the unbound proteins in the flow through and washing the resin thoroughly with PBS, bound proteins were eluted off the resin in buffer(s) containing 50-250 mM imidazole in PBS. Fractions were analyzed using one-dimensional (1-D) SDS-PAGE and IMAC3-$Cu^{2+}$ ProteinChips®.

b) Reverse-Phase Chromatography

An Agilent 1100 series HPLC system (Agilent Technologies Inc., Palo Alto, Calif.) was used for all chromatographic steps. Serum (20 µl) was processed in a buffer containing urea (final volume 0.75 ml) and then diluted 1:1 in buffer A (0.5% ACN, 0.1% TFA). 0.7 ml was loaded onto a Zorbax Eclipse® XDB C-8 column (150×4.6 mm) packed with rapid resolution 3.5 µm C-8 beads (Agilent Technologies) maintained at 25° C. at a flow rate of 1 ml/min. Proteins were eluted in a 60 min., 0-85% linear gradient of buffer B (100% ACN, 0.1% TFA) at a flow rate of 1.0 ml/min. 0.5 ml fractions were collected in an automated time based mode. Effluent was monitored at 210 nm, 214 nm and 280 nm. The column was thoroughly washed in buffer B and then re-equilibrated in buffer A between successive runs. Statistical processing and reporting of the data used ChemStation© for LC 3D (Rev. A.09.01; Agilent Technologies). Eluted fractions were dried and subjected to 1-D SDS-PAGE.

c) SDS-PAGE

Individual fractions collected by chromatography were separated using the NuPAGE™ 4-12% Bis-Tris gels electrophoresed with the XCell SureLock™ mini-vertical gel electrophoresis system (Invitrogen Life Technologies, Carlsbad, Calif.). All the samples were processed based on manufacturer's instructions. All the gels were stained using a SilverQuest™ silver staining kit (Invitrogen Life Tech., Carlsbad, Calif.).

10.1.3. LC-MS/MS Analysis

Protein bands were excised from 1-D polyacrylamide gels. Gel slices were cut into 1-2 mm cubes; washed 3× with 500 µl Ultra-pure water and incubated in 100% acetonitrile for 45 min. If the gel was silver stained, the stain was first removed with SilverQuest™ destaining solution following manufacturer's directions. The material was dried in a speed-vac, rehydrated in a 12.5 ng/µl modified sequencing grade trypsin solution (Promega, Madison, Wis.) and incubated in an ice bath for 40-45 min. The excess trypsin solution was then removed and replaced with 40-50 µl of 50 mM ammonium bicarbonate, pH 8.0 and the mixture was incubated overnight at 37° C. Peptides were extracted 2× with 25 µl 50% acetonitrile, 5% formic acid and dried in a speed-vac. Digests were resuspended in 20 µl Buffer A (5% Acetonitrile, 0.1% Formic Acid, 0.005% heptafluorobutyric acid (HFBA)) and 3-6 µl were loaded onto a 12-cm×0.075 mm fused silica capillary column packed with 5 µM diameter C-18 beads (The Nest Group, Southboro, Mass.) using a $N_2$ pressure vessel at 1100 psi. Peptides were eluted over 55 min., by applying a 0-80% linear gradient of Buffer B (95% Acetonitrile, 0.1% Formic Acid, 0.005% HFBA) at a flow rate of 130 µl/min. with a pre-column flow splitter resulting in a final flow rate of ~200 ml/min. directly into the source. The Finnigan LCQ™ Deca XP (ThermoFinnigan, San Jose, Calif.) was run in an automated collection mode with an instrument method composed of a single segment and 4 data-dependent scan events with a full MS scan followed by 3 MS/MS scans of the highest intensity ions. Normalized collision energy was set at 30, activation Q was 0.250 with minimum full scan signal intensity at $5\times10^5$ and a minimum MS2 intensity at $1\times10^4$. Dynamic exclusion was turned on utilizing a three minute repeat count of 2 with the mass width set at 1.50 Da. Sequence analysis was performed with SEQUEST™ (TurboSequest obtained from ThermoFinnigan, San Jose, Calif.) using an indexed human subset database of the non-redundant protein database from National Center for Biotechnology Information (NCBI) web site (http://www.ncbi.nlm.nih.gov/).

10.1.4. Western Blotting

The samples were analyzed by SDS-PAGE and electrotransferred onto nitrocellulose membrane at 100V for 1 h at 4° C. in transfer buffer (30 mM Tris, 150 mM Glycine, pH 8.0+20% methanol). Non-specific sites were blocked by 5% non-fat milk in TBS for 1 h. The membrane was then incubated with either polyclonal goat anti-ApoA-II antibodies (Rockland Immochemicals Inc., Gilbertsville, Pa.) or mouse monoclonal anti-ApoA-II antibodies (Biodesign Intl., Saco, Me.) in the blocker (1:3000) followed by incubation with 1:5000 dilution of anti-goat IgG HRP conjugate (Rockland Immochemicals Inc., Gilbertsville, Pa.) or anti-mouse IgG HRP conjugate (Biodesign Intl., Saco, Me.), respectively, in TBST (0.1% Tween 20 in TBS). The blot was washed thoroughly with TBST (0.1% Tween 20 in TBS) between successive incubations. Immunoreactive protein bands were detected using an ECL™ Western blotting kit (Amersham Biosciences Corp, Piscataway, N.J.). Blots overlaid with detection reagents were exposed to the ECL™ Hyperfilm™ for 1-30 sec and then developed.

10.1.5. Immunodepletion

Serum was pre-cleared of IgG by protein A affinity (Schleicher & Schuell Inc., Keene, N.H.) chromatography. Briefly, 20 μl of serum was processed in urea and diluted in PBS as previously described (Adam et al., Cancer Res, 62:3609-3614, 2002). Protein A-Sepharose resin, blocked with BSA, was thoroughly washed in urea buffer (0.45M urea in PBS). Diluted serum was incubated with 100 μl of the treated beads for 2h at 4° C. Supernatant was collected after a brief spin and the Sepharose beads containing bound serum IgG were saved. 5 μg of mouse monoclonal anti-ApoA-II antibodies (Biodesign Intl., Saco, Me.) were added to the "IgG-cleared" serum and incubated for 2 h at 4° C. Antibodies were removed from the serum using protein A-agarose beads and saved. Immunodepleted serum was analyzed by SDS-PAGE, Western blotting and SELDI.

10.1.6. SELDI-Immunoassay

Protein G coated PS20 ProteinChips® were incubated with 0.25 mg/ml mouse monoclonal anti-ApoA-II antibodies (Biodesign Intl., Saco, Me.) for 2 h at 25° C. Anti-PSA (Biodesign Intl., Saco, Me.) was used as a control. Fifty microliters of each serum sample were diluted 1:1 in 0.5% TritonX100 in PBS and incubated on the chips overnight at 4° C. Chips were washed in PBS buffers containing 1%-0.1% TritonX100 between successive incubations. For a quantitative immunoassay, 0-1000 μg/ml of ApoA-II purified from human plasma (Biodesign Intl., Saco, Me.) was added to the chips in place of serum to make a titration curve.

10.1.7. Immunohistochemistry

The method used for performing immunohistochemistry has been described extensively elsewhere (Grizzle et al., In: M. Hanausek, Walasze, Z. (ed.), John Walker's Methods in Molecular Medicine—Tumor Marker Protocols, pp. 161-179: Humana Press, Inc., Totowa, N.J., 1998; Grizzle et al., In: M. Hanausek, Walasze, Z. (ed.), John Walker's Methods in Molecular Medicine—Tumor Marker Protocols, pp. 143-160: Humana Press, Inc., Totowa, N.J., 1998). The conditions of the secondary detection method were kept constant, and then the concentrations and conditions of incubation of the primary antibodies were varied. Optimal concentrations were also tested with various antigen recovery techniques. A set of dilutions were performed using either the polyclonal (Rockland Immunochemicals Inc., Gilbertsville, Pa.) or the monoclonal antibodies (Biodesign Intl., Saco, Me.) to ApoA-II. These dilutions indicated that the optimal dilution of the polyclonal antibody was 1 to 7000 and for the monoclonal antibody 1 to 2000. Citric acid, pH 6.0 with boiling in a pressure cooker for 5 minutes was elected to use as the antigen recovery method.

The immunohistochemical approach is briefly described as follows: Five micron sections were cut from formalin fixed paraffin embedded tissues. The tissue sections were attached to slides by heating at 60 degrees for two hours, deparaffinized and rehydrated with three baths of xylene followed by graded alcohol baths from absolute to 70% and then Tris buffer. The slides were then boiled in a pressure cooker for five minutes in coplin jars filled with pH 6.0, 0.01 M citric acid, for antigen retrieval. Endogenous peroxidases were quenched with five minutes of 3% peroxide. The protein block and the secondary antibody were specific for the primary antibody used. Anti-Apolipoprotein A-II from Biodesign is a mouse monoclonal, so 3% goat serum was used for 20 minutes as a protein block, the primary antibody at a dilution of 1 to 2000 was incubated for one hour and biotinylated goat anti-mouse from Richard-Allan Scientific (Kalamazoo, Mich.) was used as the secondary detection system. Anti-Apolipoprotein A-II from Rockland Immunochemicals was a goat polyclonal and therefore, 3% horse serum was used for 20 minutes as a protein block. After one hour incubation with the primary polyclonal antibody at a dilution of 1 to 7000, a biotinylated mouse anti-goat (Sigma-Aldrich, St. Louis, Mo.) at a dilution of 1:1000 was applied as secondary antibody for 20 minutes. Streptavidin peroxidase (Richard-Allan Scientific, Kalamazoo, Mich.) incubated for 20 minutes was used as the label for both antibodies. The DAB chromagen was from a BioGenex kit (BioGenex, San Ramon, Calif.). The sections were lightly counter stained with hematoxylin, dehydrated through graded alcohols to xylene and the coverslips mounted with Permount.

10.2. Example 2

A Peak at 8943 m/z has Significant Cross Study Predictive Power

We examined data from our previously published protein expression profiling analysis of serum for the detection of (PCa) (Qu et al., Clin Chem, 48:1835-1843, 2002; Adam et al., Cancer Res, 62:3609-3614, 2002) and a more recent study involving a separate population of 186 PCa, 142 BPH and 219 NO samples using the same methods (unpublished data). We found several SELDI-TOF-MS peaks that retained discriminatory value in each of the two data sets. One of these peaks was a ~8.9K m/z peak with highly significant p-value in both populations. The 8.9K m/z peak was one of the 124 diagnostic SELDI peaks (Qu et al., Clin Chem, 48:1835-1843, 2002; Adam et al., Cancer Res, 62:3609-3614, 2002) that displayed a differential expression in the diseased vs. healthy state (FIG. 1). The intensity values for the 8.9K m/z peak were similar in the two studies suggesting that the corresponding protein is consistently over-expressed in serum from individuals with disease of the prostate. Overall the peak was most intense in the prostatic hyperplasia (BPH) and PCa. Although the greatest discriminatory value was between normal and diseased, there was some separation using the 8.9K m/z peak between BPH and PCa (Table 3). The peak retained a significant AUC (>0.62) for most of the paired tests and performed comparably in the two independent serum studies that were run two years apart indicating its consistently high significance in separating the diseased state from the normal state.

TABLE 3

Prostate Serum Study Analysis of 8.9K m/z SELDI Protein Peak

| | Group | p-Value | AUC | ‡Positive group |
|---|---|---|---|---|
| Serum Study (Year) 2000 | NO vs. (BPH + PCa) | <0.000000001 | 0.7820861678 | BPH + PCa |
| | BPH vs. PCa | 0.0000341830 | 0.6561108552 | BPH |
| Serum Study (Year) 2002 | NO vs. (BPH + PCa) | <0.000000001 | 0.8023516455 | BPH + PCa |
| | BPH vs. PCa | 0.0002874212 | 0.6337090389 | BPH |

‡Group with the 8.9K m/z intensity value greater than or equal to the cutoff value is considered the 'positive group' to compute the True Positive Ratio (sensitivity) and the False Positive Ratio (1-specificity) for each cutoff value of the peak.

10.3. Example 3

Figure 2:
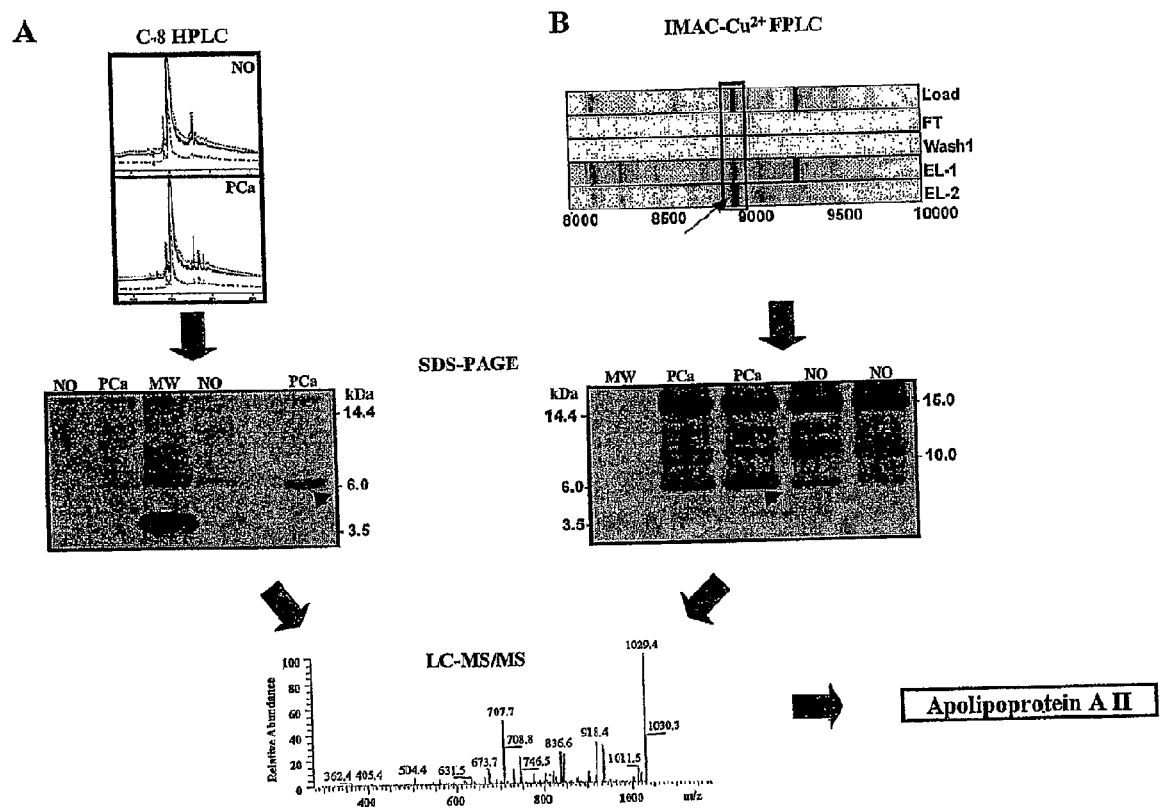
FIG. 2 shows the isolation and purification of the protein corresponding to the 8.9K m/z peak. To isolate the protein corresponding to the 8.9K m/z peak overexpressed in the diseased state, whole un-fractionated serum was either subjected to C-8 HPLC (A) or IMAC-$Cu^{2+}$ FPLC (B) followed by separation of the fractions on one-dimensional (1-D) SDS-PAGE. A protein band that migrated between the 6.0 and 10.0 kDa molecular weight markers (MW) overexpressed in the cancer samples in several independent paired tests in each of the two parallel purification schemes. The band of interest (arrowheads) was excised from each gel and identified by LC-MS/MS as mature Apolipoprotein A-II. Load: neat serum; FT: resin flow-through; EL: resin elution.

Isolation and Purification of a Protein that Corresponds to the Observed 8.9K m/z Peak In order to identify the protein that gives rise to the 8.9K m/z peak from prostate cancer specimens, whole sera were fractionated using IMAC-$Cu^{2+}$ affinity FPLC or C-8 hydrophobic HPLC in parallel (FIG. 2). We chose the two purification schemes and processed multiple sample pairs as separate mutually confirming approaches. Pairs of normal and control sera were either fractionated on IMAC HyperCel resin or C-8 reverse-phase HPLC (see Example 1) and the resulting fractions analyzed by SELDI-TOF-MS to identify the fraction(s) containing the 8.9K m/z peak. The selected fractions were then subjected to SDS-PAGE and silver staining to visualize the proteins. In each case, a protein band, with an apparent molecular weight between 6-10 kDa on the SDS-PAGE, was observed to be over-expressed in the PCa samples and was excised from the gels for analysis.

10.4. Example 4

Identification of Apolipoprotein A-II Isoform as the Protein Corresponding to the Observed 8.9K m/z Peak The differentially expressed protein bands isolated from each of the SDS-PAGE gels were subjected to tandem mass spectrometry as described. Three major tryptic fragments were obtained of m/z 1200.9 (VKSPELQAEAK) (SEQ ID NO: 1), 1157.2 (SKEQLTPLIK) (SEQ ID NO:2) and 972.6 (SPELQAEAK) (SEQ ID NO:3) with two of them overlapping in the same region. A Seques™ search of the peptides in the indexed human subset of the non-redundant protein database from NCBI identified the excised protein as being identical to an amino acid sequence found in Apolipoprotein A-II (ApoA-II).

The expected tryptic fragments of the Apolipoprotein Sequence (Id) suggest these peptides as the major feasible ions to be captured by the tandem mass spectrometer (range 400-2000 m/z). It is important to note that the same peptide ions and resulting protein identification was achieved for each of the parallel purification schemes. The same protein purification and identification procedures were repeated on multiple normal and cancer serum samples, and each time the excised protein band was identified as Apolipoprotein A-II isoform (ApoA-II isoform).

10.5. Example 5

Figure 3:
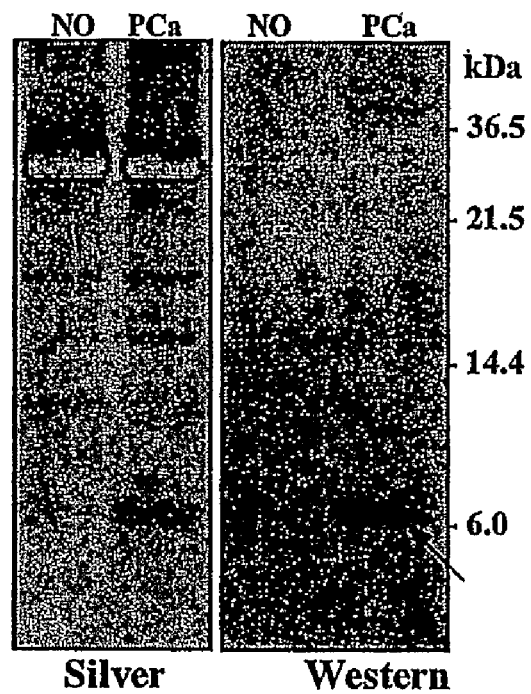
FIG. 3 shows a Western blotting analysis of serum fractions. A fraction from HPLC separation of paired samples of PCa (prostate cancer) and NO (healthy male) was subjected to SDS-PAGE followed by silver staining (left panel) or Western blotting (right panel). The differentially expressed band from the silver stained gel which was identified as Apolipoprotein A-II by tandem mass spectrometry method migrates at the same Rf as the band detected in the immunoblot (arrow).

Verification that Serum ApoA-II Isoform Gives Rise to the Observed 8.9K m/z Peak Although the identification of ApoA-II isoform as the over-expressed protein that consistently arose out of the isolation process was associated with high confidence, we needed to confirm that serum ApoA-II isoform comprises the 8.9K m/z peak observed in SELDI-TOF-MS. In order to achieve this assurance, we first verified that a polyclonal antibody specific to ApoA-II recognizes the differentially expressed band (ApoA-II isoform) by Western analysis of the serum fractions derived from the isolation/purification steps. All of the fractions examined showed a differential expression of ApoA-II isoform that coincided with the differential expression of a prominent silver stained band at the same molecular weight. In FIG. 3 we show an example of this comparison using a fraction from HPLC separation of a paired PCa and healthy male (NO). Thus, we demonstrated that the polyclonal anti-ApoA-II antibodies recognize a serum protein that is over-expressed in PCa and migrates at the same Rf as the originally targeted protein.

Figure 4:
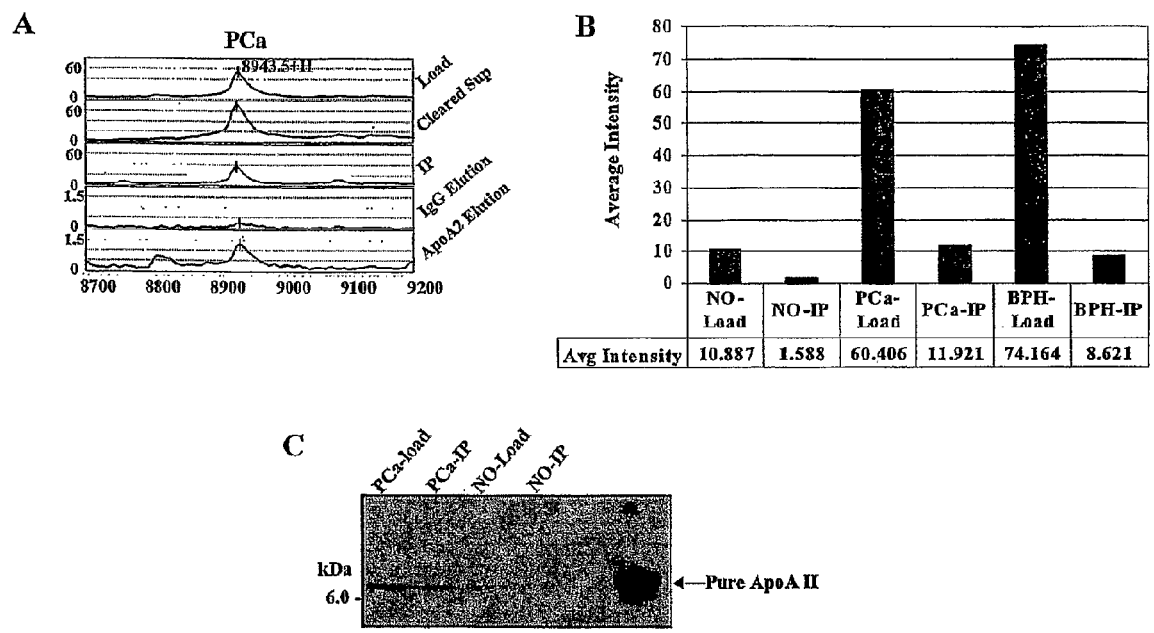
FIG. 4 shows ApoA-II immuno-depletion from serum. To verify that serum ApoA-II isoform gives rise to the observed 8.9K m/z peak on SELDI, mouse monoclonal anti-ApoA-II antibodies were used to selectively immuno-deplete ApoA-II from a set of 3 each of NO (healthy), BHP (benign prostate hyperplasia) and PCa (prostate cancer) sera. (A) Immuno-depleted PCa serum analyzed on IMAC-$Cu^{2+}$ chips. (B) A 5-fold reduction in the average intensity of the 8.9K m/z peak on SELDI platform can be seen in the immuno-depleted PCa sera. (C) Western blotting of pairs of crude and immuno-depleted PCa and NO sera with anti-ApoA-II antibodies displayed expression levels of the protein consistent with the relative intensity of the 8.9K m/z peaks observed on SELDI. Pure ApoA-II protein migrates parallel to the depleted protein bands. Load: crude serum; Cleared Sup: IgG immunodepleted serum; IP: ApoA-II immunodepleted serum; IgG Elution: IgG bound proteins; ApoA-II Elution: anti-ApoA-II bound proteins.

Since we had verified that polyclonal anti-ApoA-II antibodies were effective at recognizing a protein of the expected size, we were able to use this reagent to selectively immuno-deplete ApoA-II isoform from serum. This result was also confirmed using mouse monoclonal antibodies against ApoA-II (FIG. 4). The selective removal of ApoA-II isoform from serum should result in a loss of the 8.9K m/z peak in the SELDI-TOF-MS spectra of PCa serum. The immunodepletion studies were conducted using three separate sets of samples consisting of "pre-cleared" sera from NO, BPH and PCa as described in Example 1. In each case we compared the intensity of the 8.9K m/z peak in the (i) crude serum, (ii) pre-cleared serum, (iii) ApoA-II immuno-depleted serum, (iv) anti-ApoA-II bound and (v) IgG bound proteins. In all cases the immunodepletion significantly reduced the 8.9K m/z peak five fold inmunodepletion with a control IgG antibody did not result in any reduction of the 8.9K m/z peak.

We further examined the same fractions by separation on SDS-PAGE and immunoblotting with monoclonal anti-ApoA-II antibodies (FIG. 4C). In this analysis, the steady-state levels of serum ApoA-II isoform, as identified by anti-ApoA-II, in each of the steps of the immunodepletion were consistent with the relative amounts of the observed 8.9K m/z peaks. Furthermore, the depleted protein bands migrated with purified ApoA-II isoform on SDS-PAGE. The combined analysis using immunodepletion and Western blotting confirmed that the 8.9K m/z peak observed with SELDI-TOF-MS is most likely an isoform of ApoA-II.

10.6. Example 6

Figure 5:
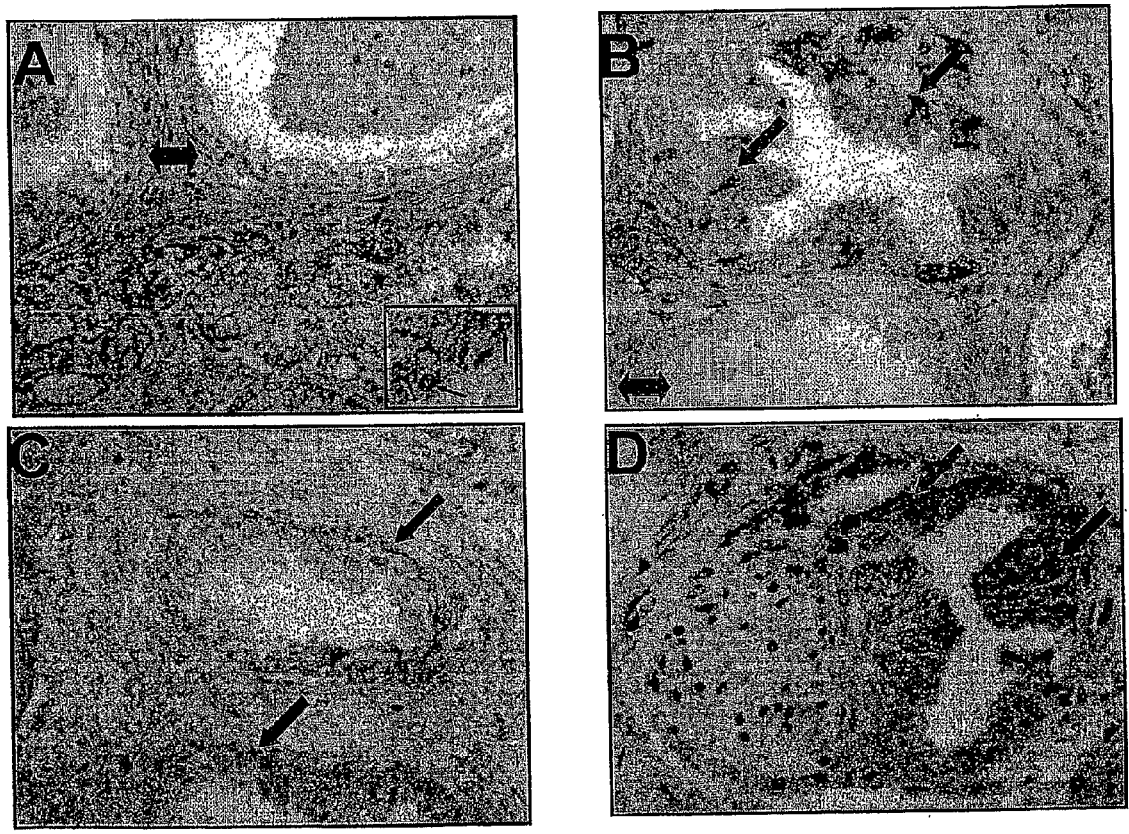
FIG. 5. Panel A: Prostate cancer infiltrating under uninvolved prostate glands (double-headed arrow) which shows minimal staining even in basal cells. The pattern of staining, which is cytoplasmic, membranous and nuclear in cancer, is accentuated slightly on the advancing edge and is variable (weak to strong). Inset shows prostate cancer demonstrating scattered nuclear (single-headed arrows) staining. Panel B: Weak to strong staining demonstrated in the luminal cells of prostatic intraepithelial neoplasia (PIN) and prostate cancer (single-headed arrows) present above uninvolved prostate glands with little staining (double-headed arrow). Panel C: Basal cells of uninvolved prostate glands demonstrating moderate staining (arrows). Endothelial spaces also show some staining. Panel D: Perineural prostate cancer with membranous and cytoplasmic staining (arrows). Original magnification X400 (A, B) and X600 (C, D).

ApoA-II Isoform is Expressed in Prostate Cancer, PIN and Prostate Basal Cells Immunohistochemistry using either the monoclonal antibody or the polyclonal antibody against ApoA-II demonstrated the same general patterns of staining. Prostatic adenocarcinoma stained stronger than other benign elements in the prostate. The pattern of staining of cancer cells was variable, primarily cytoplasmic and membranous and with rare nuclear staining (FIG. 5). Staining of the cancer cells was accentuated on the advancing edge of the tumor. Histologically normal appearing prostate glands demonstrated little staining of luminal cells, while basal cells were stained with minimal to moderate levels. The luminal and basal cells of both low grade and high grade PIN also stained variably. Fluid in endothelial and interstitial spaces also stained variably.

10.7. Example 7

Figure 6:
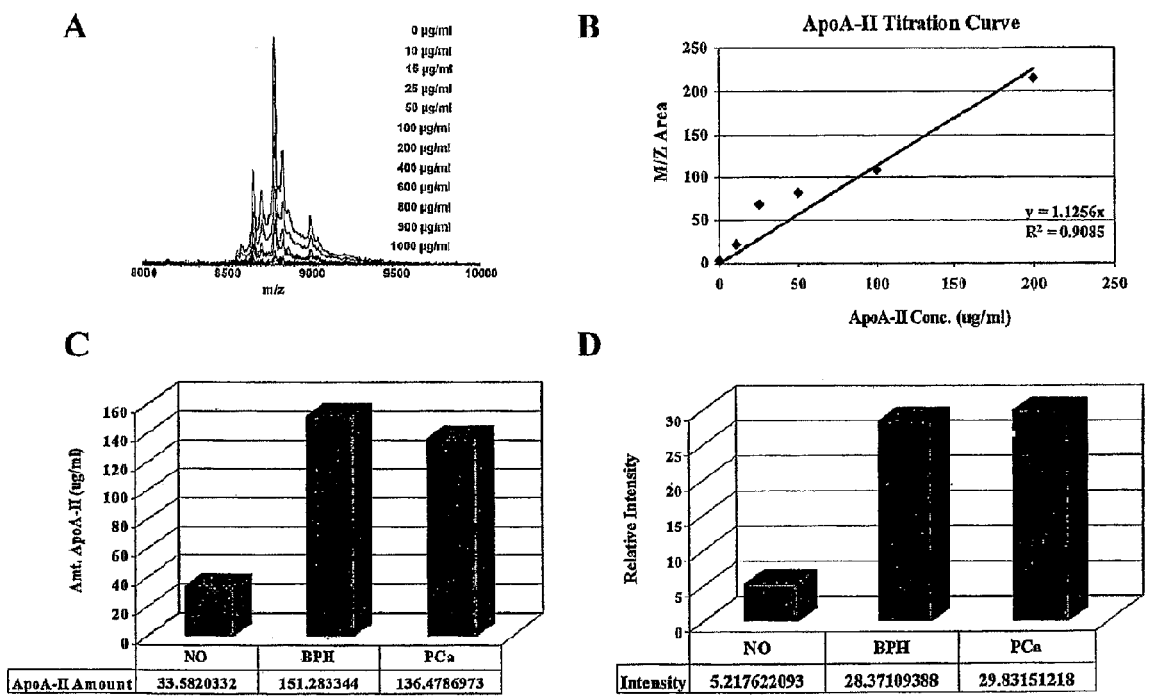
FIG. 6 shows detection of ApoA-II isoform levels in serum. A group of 50 NO (healthy), 51 BPH (benign) and 48 PCa (prostate cancer) samples were screened for ApoA-II isoform levels using the SELDI-based immunoassay on mouse mAb anti-ApoA-II coated PS20 ProteinChips®. (A) Spectra obtained from pure ApoA-II protein on the SELDI-immunoassay. The spectra are displayed in an overlayed layout for each concentration (0-1000 μg/ml). (B) The data obtained from pure ApoA-II spectra was used to establish a titration curve. (C) The 8.9K m/z area observed in the serum samples was used to calculate the serum levels of ApoA-II isoform based on the titration curve. About 4 fold increase in the amount of ApoA-II isoform in PCa samples is observed as compared to NO. (D) The relative normalized intensity observed in the SELDI-TOF-MS 8.9K m/z trace on IMAC$Cu^{2+}$ ProteinChips®.

Serum Levels of an Isoform of ApoA-II are Specifically Over-expressed in Prostate Cancer One of the outcomes of the immunodepletion study was the determination that the anti-ApoA-II antibodies were efficient at the immuno-capture of ApoA-II isoform from serum. Thus, using this antibody we developed a SELDI-based immunoassay for detection of serum ApoA-II isoform. We incubated whole serum that was prepared for SELDI-TOF-MS analysis on PS20 ProteinChip® coated with anti-ApoA-II antibodies as described in Example 1. In an initial analysis of the 8.9K m/z peak in triplicate samples of NO, BPH, PCa, the relative intensities of the 8.9K m/z peak as detected in the SELDI-based immuno-assay were comparable to the relative intensities observed for the same samples examined by standard SELDI-TOF-MS (FIG. 6).

We next established a titration curve for the 8.9K m/z peak value using purified ApoA-II isoform analyzed in the SELDI-based immuno-assay platform. Using the values obtained in the titration of purified ApoA-II isoform we then screened a group of 50 NO, 51 BPH and 48 PCa serum samples that were a part of our earlier serum profiling studies. The resulting relative amounts of ApoA-II isoform in serum as determined using the immuno-assay was comparable to the relative differences observed using the SELDI-TOF-MS 8.9K m/z trace (FIG. 6). Thus, the immuno-assay reveals that the SELDI-TOF-MS profile of the 8.9K m/z peak accurately represents the actual concentration of ApoA-II isoform in serum. With this technique, we have also demonstrated a successful immuno-assay approach for detection of ApoA-II isoform n serum.

During the establishment of the titration curve, we noted that the ApoA-II purified from human plasma (Biodesign Intl., Saco, Me.) consists of three major isoforms based upon mass differences (FIG. 6A). Although, the reported mass for ApoA-II is 8.7 kDa (Gordon et al., J Biol Chem, 258:14054-14059, 1983; Scanu et al., Biochim Biophys Acta, 351:341-347, 1974), we observed that, in the purified mixture, the 8.7K m/z peak is dominated by an 8.8K m/z peak. We also report that the 8.9K m/z peak comprises a third form of ApoA-II, also seen in the purified protein.

Figure 8:
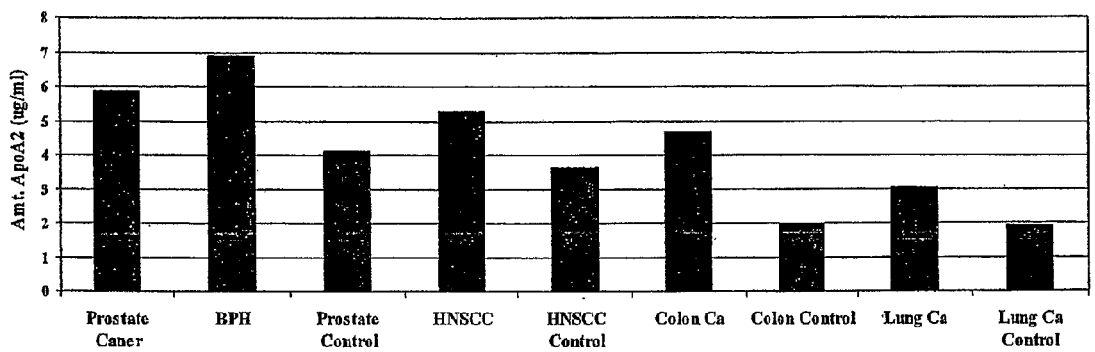
FIG. 8 shows an analysis of serum ApoA-II isoforms. The minor peaks of ApoA-II-as observed on the SELDI-immunoassay were analyzed in the serum samples from Prostate Cancer, Benign Prostate Hyperplasia (BPH),Head and Neck Squamous Cell Carcinoma (HNSCC), Colon Cancer and Lung Cancer along with their respective controls. (A) Comparative serum levels of 8.7K m/z isoform of ApoA-II. (B) Comparative serum levels of 8.8K m/z isoform of ApoA-II. Amount of ApoA-II isoforms (μg/ml) is calculated based on the titration of pure ApoA-II protein.
Figure 8:
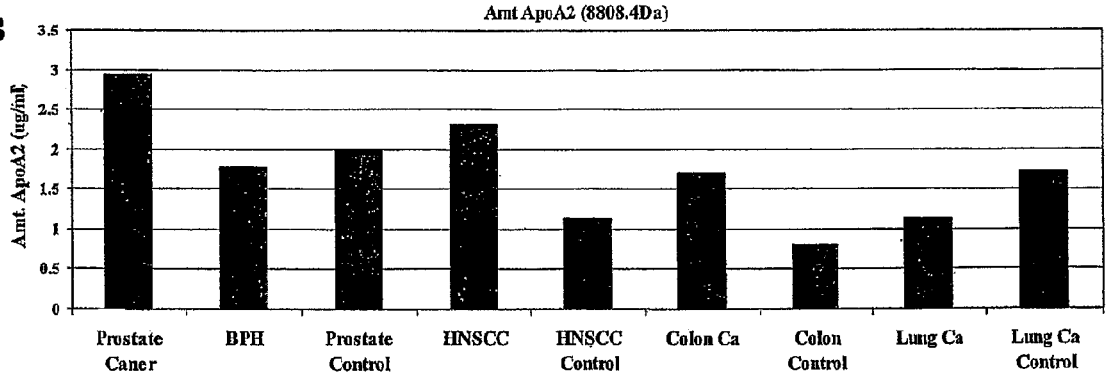

We extended the immuno-assay analysis to include cancer and control serum samples from Head and Neck Squamous Cell Carcinoma or HNSCC, Colon and Lung. In these samples, the 8.9K m/z peak was not overexpressed either in the immuno-assay or in the standard SELDI-TOF-MS analyses (FIG. 7). The values for HNSCC cancers were elevated but still significantly lower than those for either PCa or BPH. Thus, the 8.9 kDa isoform of ApoA-II is specific for PCa when compared to other common cancer groups. Interestingly, when we examined the 8.7 kDa and 8.8 kDa forms of ApoA-II in these sera, the values detected were extremely low and the correlation with either disease states was lost (FIG. 8). Contrary to the published results of the molecular weight of ApoA-II in serum, we see an 8.9 kDa form as the predominant species in sera of prostate cancer and controls and it is this form that holds a diagnostic potential in prostate cancer.

10.8. Example 8

Figure 9:
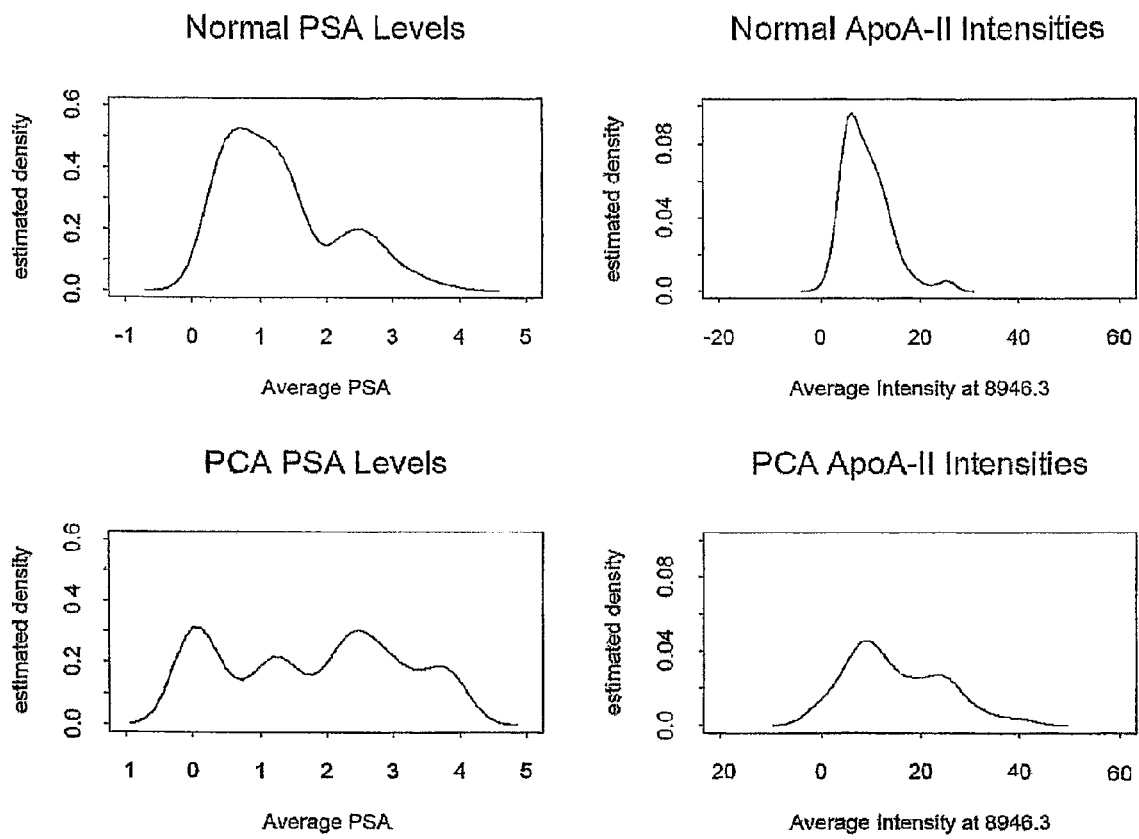
FIG. 9 shows estimated distributions of ApoA-II isoform and PSA in serum samples with low PSA. The left panels display the estimated distributions of PSA levels for sets of healthy (Normal; upper panels) samples and prostate cancer (PCA; lower panels) samples with observed PSA levels of 0-4 ng/ml. The right panels display the estimated distributions of average intensity at the 8.9K m/z peak (shown here as 8946.3) in the same set of samples (PSA 0-4 ng/ml). In all panels, the Y-axis represents the value of the estimated probability density function.

The 8.9K ApoA-II Isoform is Over-expressed in Serum from Prostate Cancer Patients in which Prostate Specific Antigen (PSA) Fails to Detect The utility of a biomarker such as ApoA-II isoform should be examined in relationship to Prostate Specific Antigen (PSA). In the present analysis, ApoA-II isoform would likely present as a biomarker with a relatively low specificity with respect to the combined non-cancer group. The difficulty in distinguishing prostate cancer from benign disease is also the case with PSA and thus ApoA-II isoform might be expected to have similar false positive rates. However, we also examined the ability of the ApoA-II isoform to discriminate cancer from controls when the PSA values are <4.0 ng/ml. In this range the ApoA-II isoform may prove a useful biomarker for contributing to the PSA test by complementing this marker in the range where PSA fails to detect cancer. Using 4.0 ng/ml as a clinical cut-off value, we analyzed the intensity of the 8.9K m/z peak in 40 cancers and 154 controls (FIG. 9). When the distribution of intensity of the 8.9K m/z peak was compared in these Normal and PCA samples (PSA 0-4 ng/ml), most of the NO samples had an average intensity between 0 and 20, while a substantial proportion of the PCa samples had an average intensity above 20 (FIG. 9). Thus, the relative intensity value of the 8.9K m/z peak was a strong discriminator even when PSA failed to detect cancer.

DISCUSSION

The development of multi-parametric diagnostic assays, for example, those that measure multiple proteins, holds tremendous promise for fulfilling clinical demands for accurate molecular analyses in modern medicine. The incorporation of expression differences of serum proteins into such a diagnostic platform may prove to be an important parameter in the realization of difficult diagnostic objectives. The identification of the individual differentially expressed proteins that comprise the diagnostic expression profile is essential to facilitating real progress in the development of a robust accurate diagnostic platform, because classic measurements of serum levels of proteins that comprise the profiles will help to stabilize/normalize the profile from patient to patient. In addition, if the proteins are identified and specific high affinity antibodies are generated to them, then more direct and potentially less expensive methods for analysis can be developed.

In fulfillment of these goals we have identified an 8.9 kDa isoform of ApoA-II as a component of a protein expression profile that detects prostate disease. ApoA-II is the second most abundant protein in HDLs (25% of protein mass) and is primarily synthesized by liver (Bisgaier and Glickman, Annu Rev Physiol, 45:625-636, 1983). The expression of the protein is regulated both at transcriptional and translational levels. In humans, ApoA-II consists of two identical 77-residue polypeptide chains linked by a disulphide bridge between Cys-6 residues with a monomer mass of 8707.9 Da (Scanu et al., Biochim Biophys Acta, 351:341-347, 1974). When we examined ApoA-II purified from human plasma (Biodesign Intl., Saco, Me.) we observed three species separated by mass; specifically we observed an 8706.5 m/z, and 8808.4 m/z and an 8943 m/z species with 8808.4 m/z being the predominant form in the purified protein. However, in the sera from healthy, BPH and PCa cases in our study, the predominant species is the 8943 m/z isoform and this is the only form specifically able to detect PCa.

ApoA-II is initially synthesized as a pre-protein composed of 100 amino acid residues, 23 residues longer than the mature protein (Gordon et al., J Biol Chem, 258:14054-14059, 1983; Tsao et al., J Biol Chem, 260:15222-15231, 1985). There is an 18 amino acid signal peptide and a 5 amino acid pro-segment which is cleaved upon secretion of the protein into the medium (Brewer et al., Proc Natl Acad Sci USA, 69:1304-1308, 1972). With respect to the expected mass of serum ApoA-II, several studies have determined that a range of predicted and observed sizes are expected due to alternative oxidization patterns, cysteinylation, sialylation and the deletion of C-terminal glutamine (Deterding et al., Electrophoresis, 23:2296-2305, 2002; Lackner et al., J Biol Chem, 260:703-706, 1985; Niederkofler et al., J Lipid Res, 44:630-639, 2003; Schmitz et al., J Lipid Res, 24:1021-1029, 1983).

Although ApoA-II is the second most abundant protein in HDLs (high density lipoproteins), its function is largely unknown. Both in mice and humans, ApoA-II influences, by an unknown mechanism, plasma levels of free fatty acids (Warden et al., Proc Natl Acad Sci USA, 90:10886-10890, 1993). In vitro studies have shown that ApoA-II can displace ApoA-I from HDL particles (Edelstein et al., J Biol Chem, 257:7189-7195, 1982), stimulate or inhibit hepatic lipase (HL) (Jahn et al., FEBS Lett, 131:366-368, 1981), inhibit lecithin cholesterol acyl transferase (LCAT) (Scanu et al., Ann NY Acad Sci, 348:160-173, 1980), and inhibit the actions of cholesterol ester transfer protein (CETP) (reviewed by Tailleux et al., Atherosclerosis, 164:1-13, 2002). The ApoA-II-deficient state has also been associated with decreased levels of plasma free fatty acids (FFA), glucose, and insulin suggesting a metabolic disturbance compatible with hypersensitivity to insulin (Weng et al., Proc Natl Acad Sci USA, 93:14788-14794, 1996). In most studies, a constant steady state level of ApoA-II is essential for maintaining homeostatic regulation of function.

In addition there is an increasing number of reports suggesting a relationship between cancer susceptibility and proteins of the lipid metabolic pathway, including Apolipoproteins (Aspinall et al., J Urol, 154:622-628, 1995; Freeman and Solomon, J Cell Biochem, 91:54-69, 2004; Lehrer, Br J Cancer, 78:1398, 1998; Myers et al., J Urol, 165:1027-1032, 2001; Trougakos and Gonos, The International Journal of Biochemistry & Cell Biology, 34:1430-1448, 2002; Zhang et al., J Urol, 159:548-554, 1998). For example, members of the Apolipoprotein family, such as Apolipoprotein D (ApoD) have been shown to be overexpressed in PCa (Aspinall et al., J Urol, 154:622-629, 1995; Zhang et al., J Urol, 159:548-554, 1998). Interestingly, a large amount of ApoD occurs primarily as a disulphide linked heterodimer of ApoA-II in human plasma (Blanco-Vaca et al., J Lipid Res, 33:1785-1796, 1992). Although the role that these proteins play in cancer is unknown, there is some evidence that they may be involved in functions of cell proliferation/apoptosis (Trougakos and Gonos, The International Journal of Biochemistry and Cell Biology, 34:1430-1448, 2002; Vogel et al., J Cell Biochem, 54:299-308, 1994). In fact, the staining pattern, which we report here for ApoA-II in normal and tumoral prostatic epithelial cells, is consistent with this suggested role.

The normal prostatic epithelium is composed of two distinct compartments, the basal cell layer and the luminal secretory cell layer. A third compartment of transiently proliferating cells has been recently described (De Marzo et al., Am J Pathol, 153:911-919, 1998). The basal cells are the stem cells of the prostatic epithelium that proliferate actively and are refractory to undergo apoptosis after castration. Consistent with this function they express the nuclear proliferation antigen PCNA, over-express the apoptosis inhibitor Bcl-2, lack expression of cell cycle inhibitor p27 and lack or express low levels of androgen receptor (De Marzo et al., Am J Pathol, 153:911-919, 1998). In contrast, secretory luminal cells are non-proliferating terminally differentiated cells, which strongly express p27, lack expression of PCNA and do not over-express Bcl-2. In addition to being the source of PSA production, benign secretory cells express high levels of the androgen receptor and undergo apoptosis after castration.

Benign prostatic hyperplastic glands demonstrate a multi-layer papillary epithelium with a prominent compartment of transiently proliferating cells in which p27 is down-regulated when compared to luminal cells. The majority of the benign prostatic glands that we evaluated here for ApoA-II expression by immunohistochemistry showed a selective or preferential expression of this protein in basal cells, variable expression pattern in multicell layer hyperplastic glands and weak to no expression in secretory luminal cells. This staining pattern correlates with those of cell proliferation markers such as PCNA (De Marzo et al., Am J Pathol, 153:911-919, 1998) and therefore, it is intriguing to speculate that ApoA-II is preferentially expressed in proliferating prostatic epithelial cells.

Furthermore, the over-expression of ApoA-II isoform reported here in PIN and invasive cancers is in agreement with this assumption. Prior studies have demonstrated cell cycle disregulation with increased cell proliferation associated with PIN and cancer, as well as progressively increasing rates of cell proliferation associated with progression of tumor Gleason's score and stage (Diaz et al., Urology, 53:931-938, 1999).

We report that by using a simple value cut-off for Apolipoprotein A-II, patients with PCa and BPH can be distinguished from healthy men as defined as randomly selected asymmetric men with PSA values <4.0 ng/ml. While an expected potential false-positive rate of ApoA-II isoform may not improve the existing capabilities of PSA, ApoA-II isoform retains the discrimination between disease and non-disease when PSA levels are <4.0 ng/ml or in other words, in cases of PCa in which PSA would have failed to detect the disease. Thus, the use of ApoA-II isoform in combination with PSA may extend the utility of this test. We are now examining samples that have PSA levels less than 4.0 ng/ml with no clinical symptoms and a normal prostate volume, to determine if ApoA-II isoform is able to detect PCa in this population. This is especially important in light of the recent results from the prostate cancer prevention trial (PCPT) showing that a significant number of advanced cancers go undetected in patients with PSA values of less than 4.0 ng/ml (Thompson et al., N Engl J Med, 350:2239-2246, 2004).

In addition to a potentially increased range of PCa detection of ApoA-II isoform compared to PSA, our results also address some of the questions being raised with respect to the eventual utility of protein expression profiling. We were able to demonstrate that the relative intensities of a m/z peak detected via mass spectrometry was comparable to the actual serum levels when the protein was measured by immunoassay. This helps to address the question of whether the platform can reflect relative quantities of some specific protein in a mixture as complex as serum. Furthermore, we provide evidence that there are m/z peaks that can be linked by conventional approaches to biological disease and demonstrate that this protein was consistently detected in two separate studies by both SELDI-TOF-MS and immuno-assay.

In addition, the over-expression of ApoA-II isoform was specific for prostate cancer and increased expression of ApoA-II isoform was not observed in cancers of head and neck, colon or lung. Thus, the expression pattern of ApoA-II isoform could be specific for prostate disease and ApoA-II isoform is neither a general cancer marker nor an artifact of mass spectrometry.

These results identify a protein peak detected by SELDI-TOF-MS that is diagnostic for PCa and BPH. The identified protein is an apparent 8.9 kDa species of the serum protein Apolipoprotein A-II, and ApoA-II isoform is specifically over-expressed in prostate cancer when compared to cancers of the head and neck, colon or lung. The correlation was observed using mass spectrometry protein expression profiling as well as mass spectrometry-based immuno-assay. The incorporation of an immune-based assay for ApoA-II isoform in conjunction with protein expression profiling may provide for a more robust assay platform than mass spectrometry alone. In addition, ApoA-II isoform may provide an important contribution to a multiplexed immuno-assay or antibody array. Since over-expression of ApoA-III isoform was also observed in patients with PCa having PSA<4.0 ng/ml, we propose that analysis of ApoA-II isoform in serum may extend the utility of current blood testing for PCa.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for screening for prostate cancer or benign prostate hyperplasia in a subject comprising the steps of:
    (a) providing a biological sample of a human physiological fluid or prostate tissue from the subject;
    (b) contacting the biological sample with an antibody capable of capturing an ApoA-II isoform comprising:
        (i) amino acid sequence VKSPELQAEAK (SEQ ID NO:1); and
        (ii) amino acid sequence SKEQLTPLIK (SEQ ID NO:2);
    (c) determining the amount of the bound ApoA-II isoform having a molecular weight of about 8943 Dalton +/−15; and
    (d) correlating the amount of the bound ApoA-II isoform having a molecular weight of about 8943 Dalton +/−15 to a status of prostate cancer or benign prostate hyperplasia.

2. The method of claim 1, wherein the screening differentiates between prostate cancer versus normal.

3. The method of claim 1, wherein the screening differentiates between prostate cancer versus benign prostate hyperplasia.

4. The method of claim 1, wherein the screening is part of a diagnosis or prognosis of prostate cancer in the subject.

5. The method according to claim 1, wherein the human physiological fluid is whole blood or serum.

SEQUENCE LISTING

```
<160> NUMBER OF SEQ ID NOS: 3

<210> SEQ ID NO 1
<211> LENGTH: 11
<212> TYPE: PRT
<213> ORGANISM: Artificial Sequence
<220> FEATURE:
<223> OTHER INFORMATION: ApoA-II isoform

<400> SEQUENCE: 1

Val Lys Ser Pro Glu Leu Gln Ala Glu Ala Lys
 1               5                   10

<210> SEQ ID NO 2
<211> LENGTH: 10
<212> TYPE: PRT
<213> ORGANISM: Artificial Sequence
<220> FEATURE:
<223> OTHER INFORMATION: ApoA-II isoform

<400> SEQUENCE: 2

Ser Lys Glu Gln Leu Thr Pro Leu Ile Lys
 1               5                   10

<210> SEQ ID NO 3
<211> LENGTH: 9
<212> TYPE: PRT
<213> ORGANISM: Artificial Sequence
<220> FEATURE:
<223> OTHER INFORMATION: ApoA-II isoform

<400> SEQUENCE: 3

Ser Pro Glu Leu Gln Ala Glu Ala Lys
 1               5
```

6. The method according to claim 1, wherein the human prostate tissue sample is a prostate cancer tissue sample or a benign prostate hyperplasia tissue sample.

7. The method according to claim 1, wherein the antibody is attached to a solid support.

8. The method according to claim 7, wherein the solid support is a mass spectrometry probe and the antibody is attached to the probe and wherein step (c) comprises detecting the bound ApoA-II isoform by mass spectrometry.

9. The method according to claim 1, wherein the antibody is selected from the group consisting of polyclonal antibodies, monoclonal antibodies, bispecific antibodies, human antibodies, humanized antibodies, chimeric antibodies, single chain antibodies, and Fv, FAb, and $Fab_2$ fragments thereof.

10. The method according to claim 1, further comprising the step of:
 (e) comparing the amount of the ApoA-II isoform having a molecular weight of about 8943 Dalton +/−15 in the biological sample with the amount of an ApoA-II isoform having a molecular weight of about 8943 Dalton +/−15 in a biological sample from one or more subjects free from prostate cancer or with a previously determined reference range for an ApoA-II isoform having a molecular weight of about 8943 Dalton +/−15 in subjects free from prostate cancer.

11. The method according to claim 1, wherein step (c) comprises high-performance liquid chromatography.

12. The method according to claim 1, wherein step (c) comprises polyacrylamide gel electrophoresis (PAGE) and Western blotting.

13. The method according to claim 12, wherein PAGE is 2-dimensional PAGE.

14. A method for screening for prostate cancer or benign prostate hyperplasia in a subject comprising the steps of:
 (a) providing a biological sample of a human physiological fluid or prostate tissue from the subject;
 (b) detecting or determining absence, presence or amount of an ApoA-II isoform, the ApoA-II isoform comprising:
  (i) amino acid sequence VKSPELQAEAK (SEQ ID NO:1); and
  (ii) amino acid sequence SKEQLTPLIK (SEQ ID NO:2);
  and wherein the ApoA-II isoform has a molecular weight of about 8943 Dalton +/−15; and
 (c) correlating the absence, presence or amount of the ApoA-II isoform to a status of prostate cancer or benign prostate hyperplasia.

* * * * *